(12) United States Patent
Lucas

(10) Patent No.: US 8,615,553 B2
(45) Date of Patent: Dec. 24, 2013

(54) INVENTIONS

(76) Inventor: John Mark Lucas, Concord, MA (US)

( * ) Notice: Subject to any disclaimer, the term of this patent is extended or adjusted under 35 U.S.C. 154(b) by 3036 days.

(21) Appl. No.: 10/901,704

(22) Filed: Jul. 29, 2004

(65) Prior Publication Data
US 2005/0086313 A1   Apr. 21, 2005

Related U.S. Application Data

(60) Provisional application No. 60/491,104, filed on Jul. 29, 2003, provisional application No. 60/501,574, filed on Sep. 9, 2003, provisional application No. 60/520,633, filed on Nov. 17, 2003.

(51) Int. Cl.
*G06F 15/16* (2006.01)

(52) U.S. Cl.
USPC .......................................................... 709/206

(58) Field of Classification Search
USPC .......................................................... 709/206
See application file for complete search history.

(56) References Cited

U.S. PATENT DOCUMENTS

| | | | | |
|---|---|---|---|---|
| 2002/0013817 A1* | 1/2002 | Collins et al. | ................. | 709/206 |
| 2002/0065892 A1* | 5/2002 | Malik | ............................ | 709/206 |
| 2003/0055905 A1* | 3/2003 | Nishiyama et al. | ........... | 709/206 |
| 2004/0064733 A1* | 4/2004 | Gong | ............................. | 713/201 |

OTHER PUBLICATIONS

'Easier e-mail', Newnan et al., Data Communications v28n4, pp. 57-64, Mar. 21, 1999.*

* cited by examiner

*Primary Examiner* — Jerry Dennison
(74) *Attorney, Agent, or Firm* — John M. Lucas

(57) ABSTRACT

The present invention relates to: an automatically adjusting seat, methods of playing video games by inputting a code that controls at least one aspect of the game, method of packaging cooking ingredients, methods and devices for providing gate and other travel information to passengers, a lid for a container and methods of reducing condensation, an email system for reducing size of user accounts, a toy figure or seat with a magnet, a receptacle with air inlets to prevent vacuum.

16 Claims, 11 Drawing Sheets

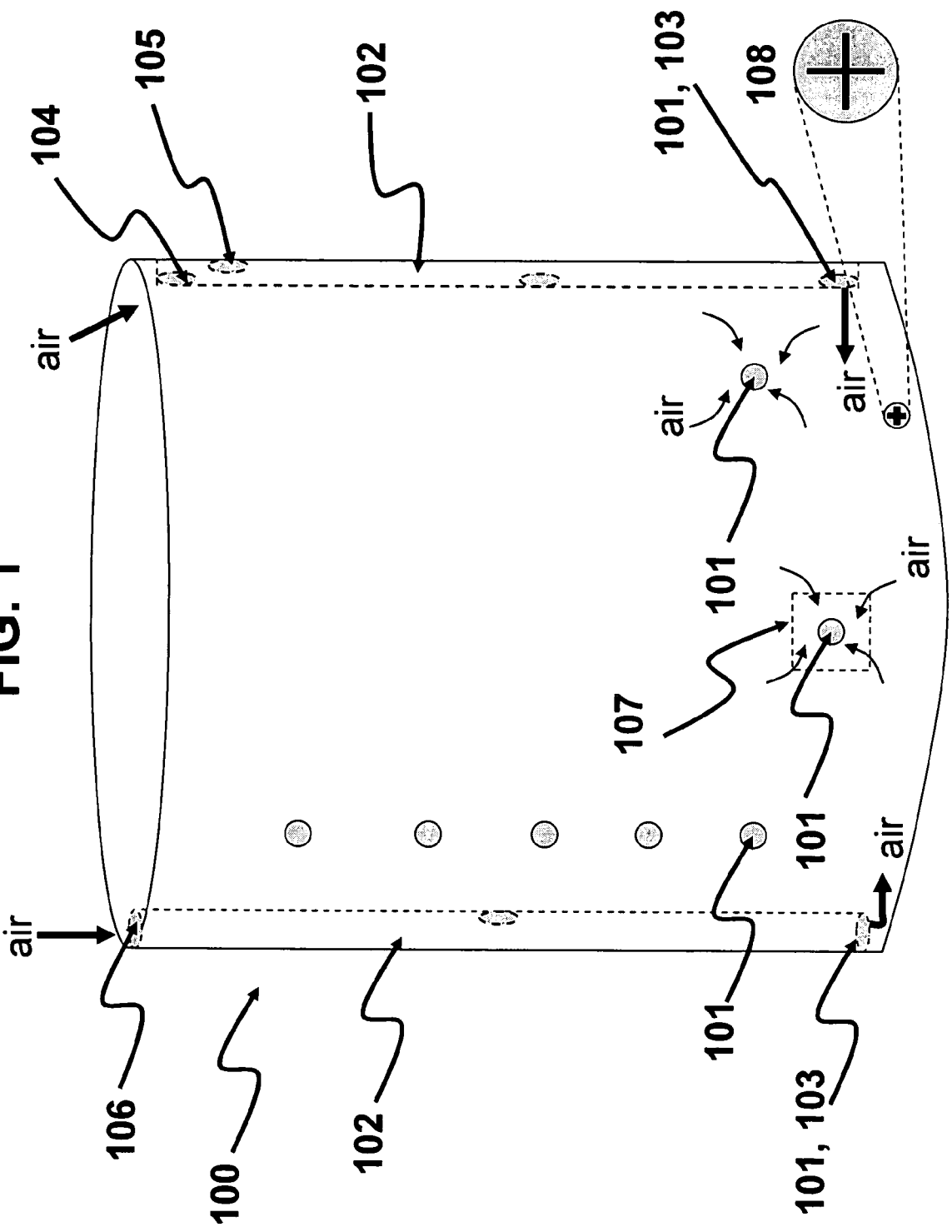

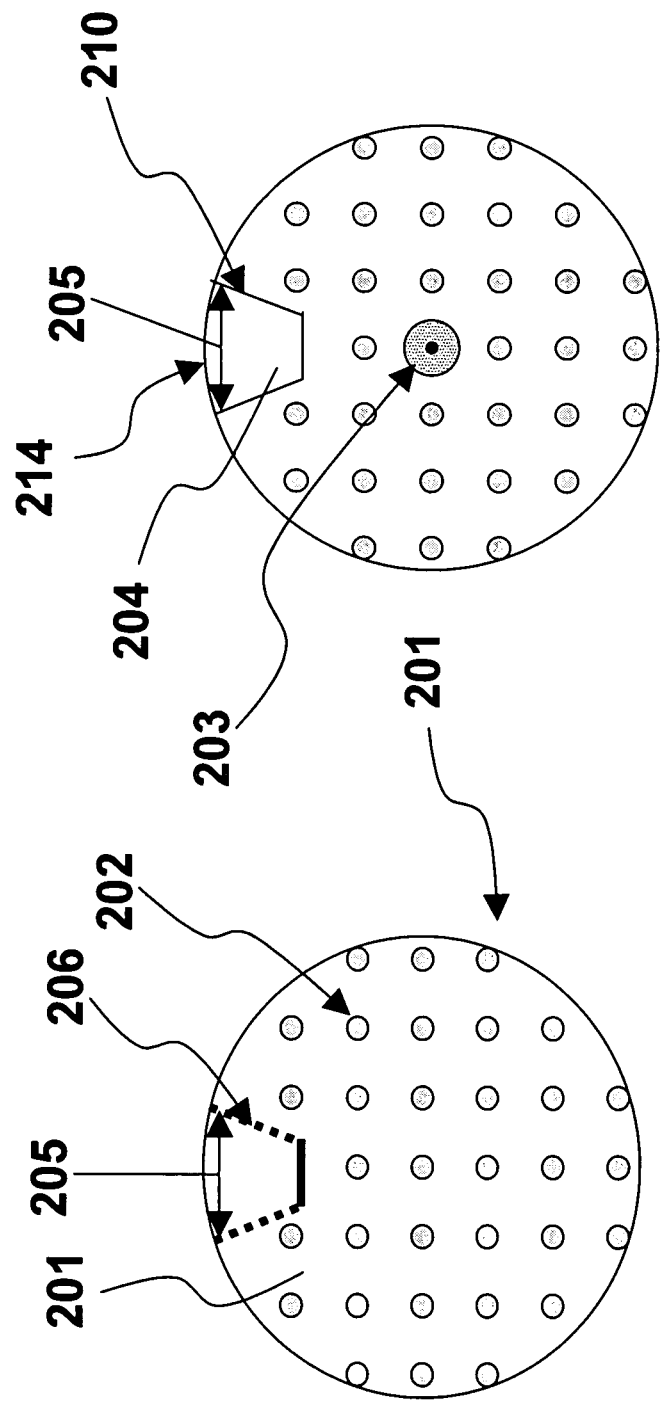

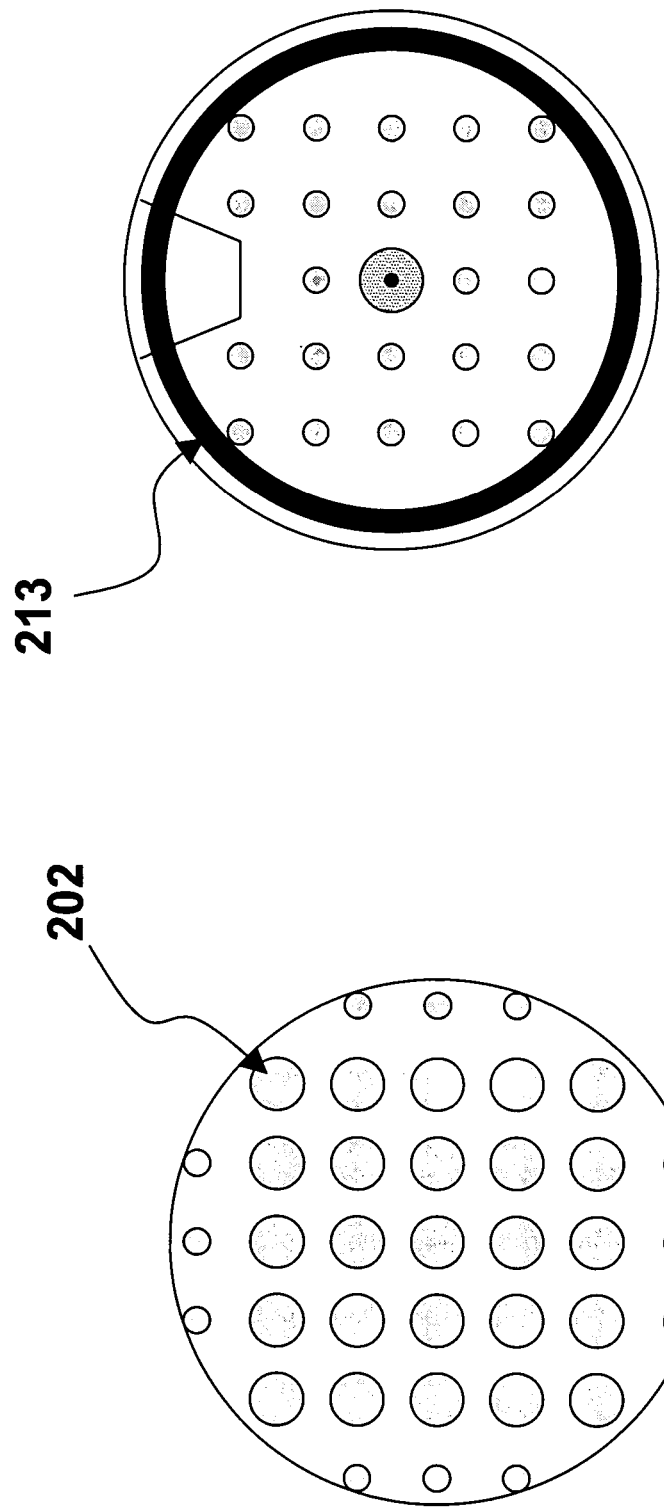

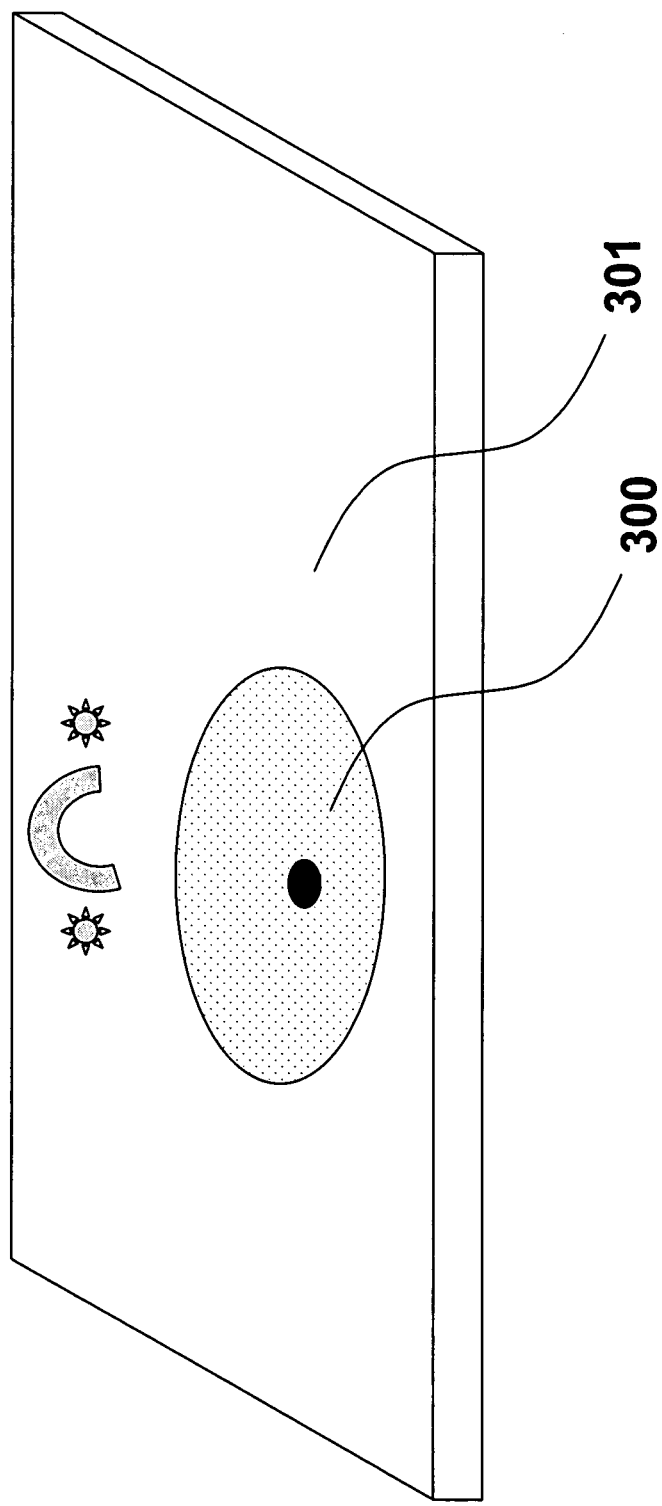

FIG. 3F
FIG. 3G
FIG. 3H
FIG. 3I
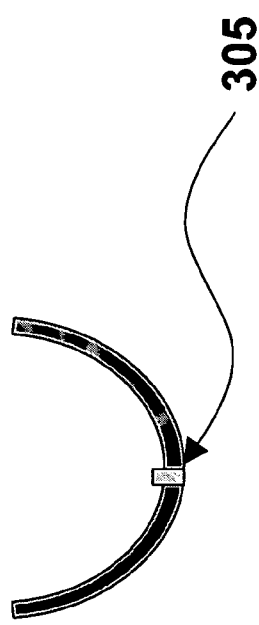
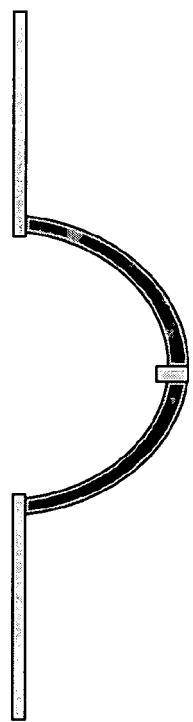

INVENTIONS

CROSS REFERENCE TO RELATED APPLICATIONS

This application claims priority under 35 USC 119(e) to U.S. Provisional Application Ser. Nos. 60/491,104, filed Jul. 29, 2003; 60/501,574, filed Sep. 9, 2003; and 60/520,633, filed Nov. 17, 2003.

FIELD OF THE INVENTION

The present invention relates to devices, articles, systems, methods of using, etc. relating to: a receptacle and method for preventing a vacuum, an automatically adjusting seat or bed, methods of playing videogames, methods of packaging cooking ingredients, methods and devices for providing gate information to passengers, a lid; an email system, a toy figure or seat with a magnet, a liner for a sink or other receptacle for creating a playful environment.

SUMMARY OF THE INVENTION

The present invention relates to: an automatically adjusting seat, methods of playing video games by inputting a code that controls at least one aspect of the game, method of packaging cooking ingredients, methods and devices for providing gate and other travel information to passengers, a lid for a container and methods of reducing condensation, an email system for reducing size of user accounts, a toy figure or seat with a magnet, a receptacle with air inlets to prevent vacuum.

BRIEF DESCRIPTION OF THE DRAWINGS

FIG. 1: Diagram of receptacle with air inlet to prevent vacuum while removing an object from a receptacle.

FIG. 2A-2F: Diagrams of lid for container for reducing condensation.

FIG. 3A-J: Diagrams of sink and liner for creating a playful environment.

DETAILED DESCRIPTION OF THE INVENTION

Figures 2E, 2F:
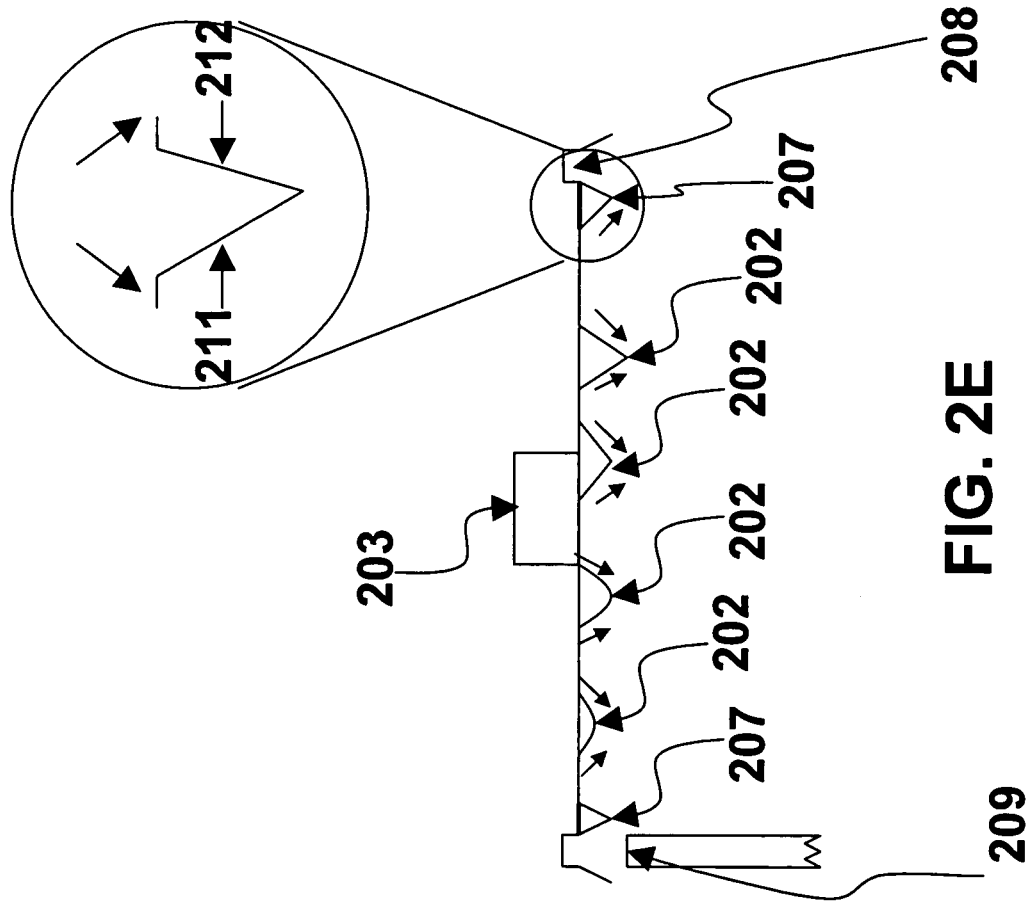

Receptacle with Air Inlet to Prevent Vacuum while Removing an Object from a Receptacle:

The present invention further relates to a receptacle or container that comprises one or more air inlets or valves in the bottom end or side (preferably at or near the bottom end) of the container (100, FIG. 1) and methods of using the same. The purpose of the one or more air inlet(s) or valves 101 is to let air into the bottom of the container when an object of nearly the same diameter as the inner space of the container is moved along the length of the container thereby creating a negative pressure (or partial vacuum referred to herein as simply a "vacuum") inside the container in the volume of space between the bottom of the inside of the container and the end of the object nearest the bottom of the container. In one embodiment the object in the container is rigid and in another it is flexible/pliable or non-rigid. In one embodiment the object is a made from plastic or other non-rigid material that can deform its shape to that of the inside of the container. In another embodiment the inner object is filled or partially filled with one or more other materials that caused the object to deform to the shape of the inside of the container. In another embodiment the inner object deforms to the shape of the inside of the container in a manner which creates a vacuum when it is pulled from the container. In one example, the container is a trash can and the object is a trash bag filled or partially filled with trash/debris. As the trash bag is pulled from the container, a negative pressure or vacuum is created that resistance to further upward movement of the bag. By providing an air inlet or valve in the bottom or side of the container, the vacuum is released and the object moves more freely because the negative pressure caused by the vacuum is reduced or eliminated.

In one aspect the container can hold at least, less than, or about 0.25, 0.05, 1, 5, 10, 15, 20, 25, 30, 35, 40, 50, 55, 60, 75, 100, 125, 150 gallons of water or between about 0.25-1, 1-5, 5-10, 10-20, 20-30, 30-40, 40-50, 50-60, 60-70, 70-100, 100-150 gallons of water.

In one embodiment the air inlet is a one-way valve that allows air into the container but does not allow air or liquids, such as contaminated water, to readily flow out of the container. In another embodiment the one-way valve allows air into but not liquids such as water to readily flow into the container. In one embodiment the valve is fluid tight when not under a differential pressure. In one embodiment, the air inlet (with or without a one- or two-way valve) passes directly through the side or bottom of the container. In another embodiment the valve is a two-way valve that will allow air to enter the container in either direction. In one embodiment the inlet is simply a hole. In another embodiment the valve is a pressure sensitive valve that opens when atmospheric pressure on the outside of the container is greater by a certain amount than the pressure on the inside of the container. That is, when a negative pressure is created on the inside of the container. Preferably, for a one-way valve of the invention, when the pressure is negative (less than atmospheric) on the inside of the container, the positive pressure on the outside of the container overcomes a force holding the valve closed and the it opens, typically allowing normal atmospheric air to enter the system (i.e., the container), thereby eliminating the negative pressure. In one embodiment the valve is a simple air valve with a spring holding it shut. In one embodiment the valve is a simple slit valve which may be in the form of a cut or perforated rubber/plastic septum. In one embodiment the slit is a single slit, an X shaped slit, a star/asterisk shaped slit, a three sided box shaped slit, or other shape.

When a vacuum is created, the air-pressure on the outside of the container pushes the valve, e.g. slit, open allowing air into the container. When the vacuum is reduced or eliminated the valve closes. When closed, the valve is preferable air or water tight or nearly so or at least does not permit air to readily flow in and out of the container. The type of material used and the design of the valve is preferably such that the pressure needed to open the valve is equivalent to the pressure created when a vacuum is created.

In one embodiment the one- or two-way valve opens with at least 0.25 lb, 0.5 lb, 1 lb, 2 lbs, 3 lbs, 4 lbs, 5 lbs, 6 lbs, 7 lbs, 8 lbs, 9 lbs, 10 lbs, 12 lbs, 15 lbs, 17 lbs or at least 20 lbs of pressure per square inch. In one embodiment, the container is a trash can and the pressure needed to open the valve is less than that caused by the vacuum created when a plastic bag of trash is lifted upward from the container.

In one embodiment, the slit or inlet opening is held in its closed position by the resilient properties of the material although it is adapted to be moved into its open position against the resilient bias force of the material by a predetermined differential positive pressure exerted on one side of the membrane member which occurs when a vacuum is created on the inside of the container. In one embodiment, the slit valve is of the type described in U.S. Pat. No. 6,450,375, incorporated herein in its entirety, adapted such that the apex created by the peripheral wall portion of the base member and an adjacent wall is facing the inside rather than the outside of the container. Moreover, in addition to being inserted "backwards" the valve is inserted into the bottom or side of the container rather than acting as a lid or cover. Briefly, the slit closure valve includes a membrane member of flexible material having an at least unidirectionally aligned slit-like inlet opening and a base member peripherally surrounding the membrane member and connected to the membrane member. The inlet opening is held in its closed position by the resilient properties of the material although it is adapted to be moved into its open position against the resilient bias force of the material by a predetermined differential positive pressure exerted on one side of the membrane member which occurs when a vacuum is created on the inside of the container. A peripheral wall portion of the base member and an adjacent wall portion of the membrane member include therebetween an acute angle of less than 90'. The valve thereby enables the pressure between the interior of a container and its surroundings to be equalized or more nearly when a vacuum is created inside of the container.

In another embodiment the air inlet is a tube or other hollow structure 102 that spans the length of the container, or at least 10%, 20%, 30%, 40%, 50%, 65%, 75%, 80%, 85% 90%, 95% or 97% the length of the container from bottom to top. In one embodiment the hollow structure is sealed or substantially sealed except at the two ends of the structure.

In another embodiment the hollow structure has one, two, three, four, five, or more additional holes along the length of the structure. The structure may even be a mesh or other perforated structure as long as there is a portion that allows air access to the bottom or side of the container where a vacuum would otherwise form but for the air inlet. In one embodiment the hollow structure is open at or near the bottom inside of the container 103. In another embodiment the opposing end is at or near the top, or opening, of the container. In an embodiment the open end 104 of the hollow structure at the top opens to the inside of the container. In another embodiment the open end 105 of the structure at the top opens towards the outside of the container. In a third embodiment the open end of the hollow structure at the top opens towards the open end of the container, i.e. points upwards or towards the top 106. A structure that opens at greater than 45 degrees to the length axis of the container and towards the opening of the container is preferred because is will help prevent the opening from being sealed as the object is removed from the container. The hollow tube can be on the inside, outside or as part of the side wall of the container as long as there is an opening at or towards the bottom and at or towards the top of the container such can air can flow into the bottom or side of the container. It is also preferred that the opening of the structure at the top of the container is positioned such that it is covered or is within the inside of the container when a lid for the container is placed on the container. This is particularly advantageous when the container is a trash can because it prevents smells from escaping the receptacle. The container may contain a multiplicity of structures to provide air access over multiple locations.

Another embodiment relates to a foot pedal operated trash such as the kind whereby a lid is opened when the pedal is depressed. In this embodiment, depressing the foot pedal opens an air inlet in the trash can. In another embodiment depressing the foot pedal opens both a lid and air inlet. Opening an air inlet with a foot pedal can be carried out, for example, by a cover or slide plate 107 over an opening in the container that slides away from the opening 101 when the foot pedal is depressed. Other well known methods are known in the art for other uses that can be readily adapted for the use of the present invention.

In a specific embodiment, the invention relates to a method of removing trash from a trash can said method comprising the steps of: obtaining a trash can comprising one or more air inlets or valves on the bottom or side of said trash can, filling said trash can full or partially full with trash, emptying said trash can. The method further comprises the steps of inserting a trash bag into said trash can, and emptying said trashing can by turning said can upside down or at an angle sufficient such that trash bag falls from can or by lifting upwards on said bag until it is free from said can.

Method of Reducing the Size of Email Accounts:

Data file attachments greatly increase the size of an email account. Removing attachments and resaving attachments is time consuming. Sending a pathway or link to a saved file is time consuming and can be troublesome because the recipient must have access to the saved file. Both the sender and recipient must also have shared access to the same folder. Moreover, for files where privacy is a concern, there should be no third party access. The sender may have to send a different link to each recipient receiving an attached file. Finally, the sender and recipient may not have shared access to a folder. This is especially a problem where the sender and recipient are not on the same internal or local area network or where the sender does not have access to the recipient's file server.

Figure 4A:
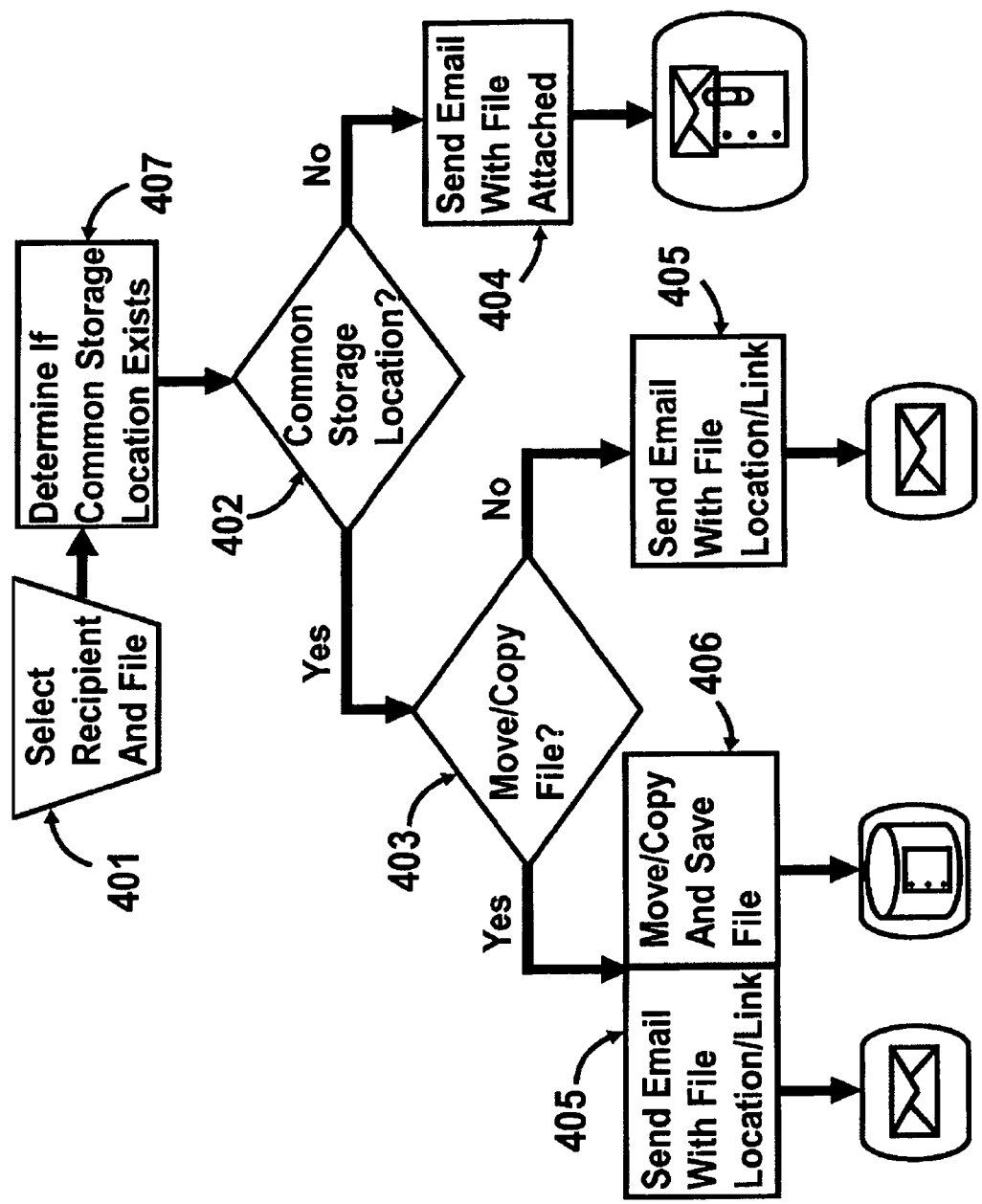
FIG. 4A-B: Diagrams of system for reducing size of email accounts.
Figure 4B:
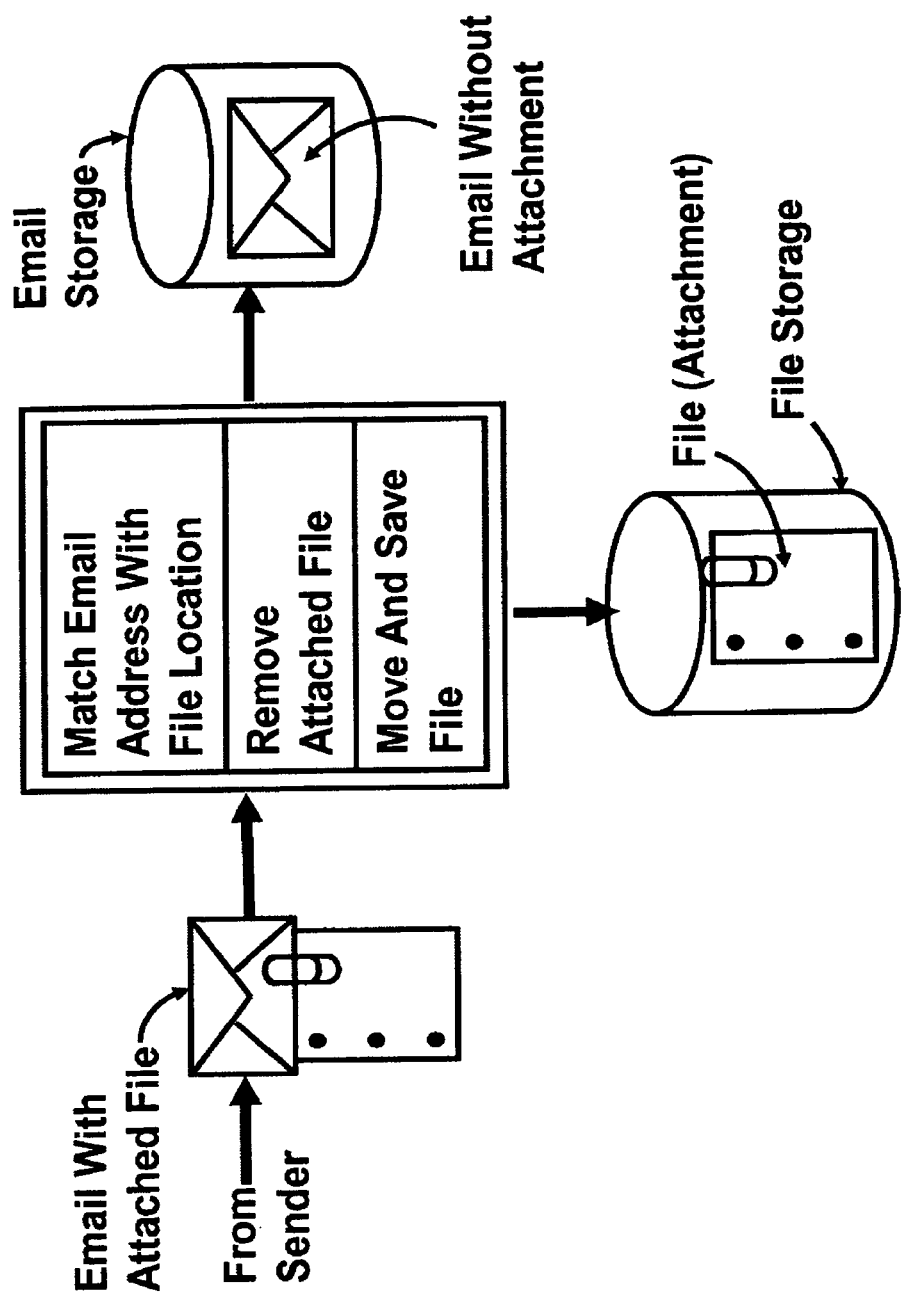

The present invention overcomes these problems by providing a system and methods for reducing the increase in size of an email account, wherein an attached data file sent in an email that would otherwise be delivered as an attachment to the intended recipient is instead substituted with either a) a pathway or link or, b) a notice that a file has been made available for access by sender for recipient, before reaching an inbox of a recipient (FIG. 4A-B). The link automatically directs a user to a file location where the attached file is saved allowing access to the file. Depending on the identity of the recipient the email system generates a link for a recipient or sends the attached file to the recipient depending on the situation. In one embodiment the date file type is selected from a document or text file, a spreadsheet, a presentation, a video file, an audio file, a database file, an audio and video file or combination thereof. Each data file type may also be specifically excluded from the present invention. In one embodiment the sender or recipient may choose which type of data file, selected from above, that may or may not be substituted with a link in an email message. The attached file is normally saved as the same file type as when it was selected by the sender, i.e., the file type or three letter extension remains the same. Unless specifically set forth, the file is not saved as an email program file type, e.g., a "*.pst" file.

In the present invention, a sender chooses a recipient and a file he wants the recipient to have access to 401. The sender may go through the same procedure as when sending an actual attached file, i.e., selects a file for intersection or attachment to the email. Rather than send the email with an attached data file to each recipient, the email system will instead send a link to the file for selected recipients 405 and send the actual file to other recipients 404. Once the file is selected the email system creates a link to the file for which the recipient will have access 405. In one aspect the email system will move or copy and save the selected file to a new location 406. The email system may move or copy and save the selected file to one location or it may move or copy and save the file to more then one location depending on whether all the recipients are to have access to the same file in the same location or each recipient has access to a copy of the file that is saved at a location unique for each recipient 407. Thus for a selected file, each of two or more recipients may receive the same or a different link. Where each recipient receives a different link, each link is for the same file but the file is saved at a different location corresponding to each link.

Depending on the embodiment, the file selected by the sender may be moved, copied and saved, or remain in the same location as when it is selected by the sender 403. The file may be moved or copied and saved, for example, to a shared folder. The user privileges of the sender and recipient may be the same or different. The sender may have privileges comprising any combination of: read, write, create, modify, file scan, or delete privileges. The recipient may also have privileges comprising any combination of: read, write, create, modify, file scan, or delete. The privileges of the sender and the recipient need not be the same. For example, the recipient may have read only access to a file selected by a sender thereby preventing the recipient form moving, modifying or deleting the file. The recipient may be able to copy the file thus allowing the recipient to move, modify or delete the file as he chooses. In one embodiment, once a selected file is copied by the recipient, the file is deleted.

The file may also be moved or copied and moved to the hard drive on the recipient's or other third party computer or copied and saved to a different location on the sender's computer. In one embodiment the recipient will have access only to the file selected by the sender rather than to an entire folder. In another embodiment, the sender may limit the amount of time the recipient has access to the file.

The moving or copying and saving of the file to a different location than where it was when selected may be executed by the email program or a program associated with the email program or email server.

In one aspect, in cases where both the sender and the recipient have access to the file, once the email is sent to the recipient with the link for the file, the sender is notified that the file is linked to recipient when the sender attempts to move, delete, open or modify the file. The sender may be prevented from doing the same. In one aspect the link is directed to a file on the sender's hard drive or a sender's folder on a network server. In another aspect the file is moved or copied to a shared folder.

In one aspect the selected file is moved or copied and moved to a folder that is not shared by the sender and recipient, i.e., one of the parties has no privileges to the folder where the file is located. In this embodiment the email system or the recipient chooses the location where the selected file is to be saved and is not revealed to the sender. Thus, the link to the file may not be shown in the sender's copy of the message in a "sent" folder. However, in one embodiment the link to the file is encoded in the sent message and revealed to the recipient if resent to the recipient. This is useful in cases where the recipient requests another copy of the email because he has deleted his copy or cannot find the email or saved file.

In another aspect an email is sent to multiple recipients wherein one or more of the recipients is sent a link and one or more is sent the actual file attached. A recipient may be sent the actual attachment when the recipient is outside the internal network, has restricted access to the internal network or where the sender and recipient do not have shared or complementary (e.g., the sender has permission to save files and the recipient has permission to read files) access to a file server or hard drive 404. In this aspect the email system determines whether a recipient receives a link or the actual file attached 402. Thus, the sender's sent message contains the actual file attached. The sent message may contain a link rather or an attached file. The link may be the same or different than a link received by two different recipients depending on whether the sender and recipients have shared or complementary access to a file server or hard drive.

Where the selected file is copied and saved to a new location by the email system, the sender may or may not be informed where the new location is. A copy of the sent message in the sender's send mailbox may or may not indicate the link sent to the recipient.

The email message the recipient receives contains a link to the file selected by the sender. In one embodiment the link is an active link such that the recipient can directly access the selected file through the email message, for example by clicking on the link with the mouse cursor.

A lookup table is provided to link an email address with a folder location for saving attachments. The selected file may be attached and sent to recipient and diverted to a folder after it is sent but before it is delivered to the recipient mailbox or diverted to a folder after it is sent and received into the recipient's mailbox. Thus, at some point in the message's pathway to the recipient's mailbox, the attached file is stripped from the message and redirected to a selected folder. If the attached file is encoded, for example into ASCII text, for transmission purposes, at some point before the attached file is saved to the selected folder the attached file is decoded or retranslated back into its original file type. As discussed herein the selected file may also be saved to a folder without ever being attached.

Another aspect of the present invention includes an email system that automatically removes attachments from incoming email messages and saves them to a separate location (not in the recipient's email account), for example, either on the user's computer, on a file server (It is noted that a server may contain both an email and file server. In this case the file is saved from the email dedicated portion of the server to the file server portion of the server) or other location (FIG. 4B). In one embodiment the attached file is replaced by a link to the saved file. In another embodiment the link is an active link allowing the recipient to directly access the file through the email message, e.g., by clicking on the link with the mouse cursor. In this aspect of the invention the sender attaches and sends an actual file thus the replacing of the attached file in the email message occurs only on the recipient's side or at least independent of what occurs on the sender's side.

In one embodiment, the email system only removes and saves specific types of attached files. The recipient may be able to select the type of attached files that may or may not be removed from an email message and saved. In one embodiment the file type is selected from a document or text file, a spreadsheet, a presentation, a video file, an audio file, a database file, an audio and video file or combination thereof. Each data file type may also be specifically excluded from the present invention.

Specifically excluded from the invention are methods where the attached file is a voice file and is saved to a voice mail system.

The system of the invention comprises the following components:

(1) an email server, such as simple mail transfer protocol (SMTP), for sending mail, and post office protocol 3 (POP3) for receiving mail;
and one or more of the following:
(2) a processing mechanism which generates a pathway or link for a selected file and inserts said link into an email message;
(3) a database which links an email recipient address with said processing mechanism;

(4) a system for determining whether a recipient is on the same local network or whether sender and recipient have a shared access at any location (folder) (e.g., sender's computer, recipient's computer, sender's network or recipient's network) or at least a common location where sender can save a file and recipient can access a file;
(5) a system for matching a sender or recipient with a location (folder) for saving attachments;
(6) a system for moving or copying files to a location (folder) matched with a recipient, matched with a sender, or matched with a combination of both a recipient and a sender;
(7) a system for removing an attached file from an email message, saving the attached file to a new location, and optionally replacing the removed file with a link to the new saved location.
(8) a system for directing a program to open a file from a saved link location.

The invention includes server hardware and software which performs the following functions:
(1) monitor the sending of outbound and arrival of inbound email messages;
(2) identify selected files;
(3) move and save, or copy and save, identified selected files to a second location, wherein the second location is not on the email server or not saved as an email program file type, e.g., a "*.pst" file;
(4) identify whether a recipient is an authorized user of the local network, Example 1:

A sender of an email wishes to send an email message with a document to three recipients. One recipient is outside the network and the other three are inside the network. The sender writes an email message and follows the necessary directions to attach a file. The email system copies the file to the message sent to the outside recipient. The second recipient has set his email account up to receive all attachments so he too receives the document. The third recipient receives the message with a link. The recipient clicks on the link and the file is opened with the appropriate program. At the time the file was sent to the third email recipient, the email system copied and saved the document to a new location corresponding to the link. The sender has his email options set up to save his sent files. His system allows him to save the files sent to recipients or to save only a link to the file. The sender has his options set to save a link only to the sent email is saved with a link only. The email indicates which recipients were sent the actual file and which were sent links. The sent email also shows the links to the file as seen by the recipient, except for the forth recipient who has his email account options set to block the sender from seeing where the file was copied and saved. The sender thus knows that his email system copied and saved the selected document to a location accessible by the recipient but not where. The forth recipient inadvertently deletes the email and requests the sender to resend, which the sender does. Although the sender was unable to identify the link and the location where the file was saved, this information remained embedded in the sent message so the information was not lost.

Saving Files Opened as Attached Files:

The present invention further relates to a program, either the email client program (an example of an email client is Microsoft Outlook®), or the program running the attached file (an example of such a program is Microsoft Word®), that requests a location for the file to be saved by the user when the user attempts to save the file. For example, currently when saving a Word® file that was opened from an attachment of an email in Outlook, no request for a file location is made when the user chooses the save function. When the user exits the Word file, any changes are lost. This does not occur when the user chooses the "save as" function rather then the "save" function. In the present invention, the "save" function would act or work in the same or similar manner as the "save as" function when a file that is opened from an attachment is saved. In one embodiment the email client is Microsoft Outlook, the attached file is opened in Microsoft Word, and the file is saved after changes to the file has been made by the user.

Automatically Adjusting Seat or Bed:

The present invention relates to a seat or bed that automatically adjusts its position on a continual basis, either continuously or at continually repeating time intervals. In an aspect the seat is for a vehicle, e.g., car, truck, tractor trailer, suv, bus, boat or plane. The invention is useful for any seat or bed where it is desirable to change positions, either continuously or from time to time, particularly when one has to remain seated or lying down for an extended period of time. For example, the present invention is useful for improving the comfort of a person driving a long distance. The invention can reduce the length of time a portion of the body is exposed to an amount of pressure that can cause discomfort, reduced circulation or nerve impingement and lead to disorders such as bed sores (ulcers). The invention thus includes methods for reducing these discomforts and disorders.

When a person sits in a seat (e.g., chair, couch/sofa, recliner, etc.) or lies in a bed, body weight is normally not distributed evenly. Rather there are pressure points or areas of increased pressure. This is due to a combination of posture, anatomy, and seat/bed conformation. Thus, by changing the confirmation of the seat/bed, pressure is shifted to other parts of the body.

Currently, there are seats/beds that are adjustable either manually or electronically using motors. These seats adjust while the person sitting/lying is inputting signals, e.g., push a button or lever. Once the person ceases inputting signals to the seat, the seat no longer adjusts its position or ceases to adjust after completing a single adjustment.

There are also seats/beds that will automatically return to a pre-set position. This is useful when there are multiple users of the same seat (e.g., multiple drivers of the same vehicle) or users of the same bed. There are also seats and beds that move to a preset position once a control (e.g., button) is activated. These seats differ from those of the present invention in that they do not adjust continuously or on a continually repeating basis and are thus excluded from the present invention.

In one embodiment the present invention relates to automatically adjusting seat or bed, wherein said seat or bed adjusts its position either continuously or at multiple repeating intervals, and further wherein positional adjustments occur after the user discontinues to input signals into a control device directing movement of said seat or bed or after the seat or bed completes a single series of adjustments in response to user discontinues to input signals, and wherein said positional adjustment is not in response to feedback from a pressure sensor.

For the seat/bed of the present invention, after an initial signal input, the seat/bed will automatically adjust its position either continuously or at continually repeating intervals. In one embodiment, seat/bed movement is not in response to a pressure sensor feedback mechanism. In one embodiment, seat/bed adjustments are made either continuously or at continually repeating intervals both in response to pressure sensor feedback and not in response to feedback from a pressure sensor. For seats that adjust continuously or at continually repeating intervals the rate of movement in seat position may be imperceptible by the occupier or perceptive only upon concentration. Of course, the movement may also be perceptible. In an aspect the seat may move les than 10 cm, 8 cm, 6 cm, 4 cm, 2 cm, 1 cm, 7 mm, 5 mm, 3 mm, 1 mm or less than 1 mm per minute. For repeating interval adjustment the time between adjustments may or may not be the same depending on the embodiment. The time between adjustments may be at least once every 10 sec, 20 sec, 30 sec, 45 sec, 1 min, 2 min, 3 min, 5 min 7 min, 10 min, 15 min, 20 min, 25 min, 30 min, 35 min, 40 min, 45 min, 50 min, 55 min or 1 hr. For continual adjustment, the motion may be continual, e.g., for at least 10 sec, 15 sec, 30 sec, 1 min, 5 min, 10 min, 15 min, 30 min, 1 hr, 2 hr, 3 hr, 4 hr, 5 hr, 6 hr, 7 hr, 8 hr, 12 hr or longer; with or without repeating operations. For repeating adjustments, the number of repeating adjustments resulting from a single activation or input from the controller may be, e.g., at least 2, 5, 10, 15, 20, 25, 50, 75, 100, 250, 500, 1000, or at least 10,000 repeating adjustments.

Multiple aspects of a seat/bed position may be adjusted including but not limited to head position, neck position, upper back position, lumbar position, seat height, seat bottom angle, seat back angle, head rest height, head rest angle, seat forward/backwards, seat width, seat bottom firmness, seat back firmness, bed firmness etc. for a driver's seat further adjustments include break, clutch, accelerator pedal forward/backwards or up/down or angle, steering wheel forward/backwards, up/down or angle up/down, minor left/right or up/down angle are included. Pedal, steering wheel and mirror adjustments may be included in addition to the seat position adjustment since their adjustment position may need to change when the change in seating position becomes great enough. In one embodiment the pedal or steering wheel or mirrors move in proportion to the seat. In another embodiment they do not move in proportion to the seat. Pedal, steering wheel and mirror position likewise affects the seating position of the occupant, thus the invention further relates to a pedal, steering wheel or mirror that adjust automatically in the same fashion. In one embodiment the pedal, steering wheel, or mirror move in direct relation to the seat such that the distances between key points remains about the same. For example when a seat moves back the pedals move forward by the same amount or a proportional amount. In one embodiment the distance between two points remains about the same. The two points may be for example, the distance the steering wheel and a position on the seat such that the positions between the steering wheel and shoulder joint or the distance between a pedal and the hip or knee joint remain relatively constant. In another embodiment the pedal, steering wheel or mirror either do not adjust automatically or do not automatically adjust in proportion to the seat.

In one aspect the seat position will not vary over the entire range of motion for a seat/bed aspect. Each aspect, e.g., lumbar, seat height, seat bottom angle, seat back angle, head rest height, head rest angle, seat forward/backwards, seat width, seat bottom firmness, seat back firmness, break pedal forward/backwards, clutch pedal forward/backwards, accelerator pedal forward/backwards or up/down or angle, steering wheel forward/backwards, up/down or angle up/down, minor left/right or up/down angle, can vary by about 1, 2, 3, 5, 7, 10, 15, 20, 25, 30, 35, 40, 45, 50, 55, 60, 65, 70, 75, 80, 85, 90, or 95% of the positional range. The percent range for each aspect may be independent or differ from one another or two or more aspects may vary by the same amount. In another embodiment one may select the amount or range of change in seat position as some occupants will want the seat position to vary a great deal while others will prefer less variance.

In another embodiment one may select any one or combination of aspects selected from lumbar, seat height, seat bottom angle, seat back angle, head rest height, head rest angle, seat forward/backwards, seat width, seat bottom firmness, seat back firmness, break pedal forward/backwards, clutch pedal forward/backwards, accelerator pedal forward/backwards or up/down or angle, steering wheel forward/backwards, up/down or angle up/down, minor left/right or up/down angle, or other aspects. For example one may maintain a constant position of any one or combination of aspects selected from lumbar, seat height, seat bottom angle, seat back angle, head rest height, head rest angle, seat forward/backwards, seat width, seat bottom firmness, seat back firmness, break pedal forward/backwards, clutch pedal forward/backwards, accelerator pedal forward/backwards or up/down or angle, steering wheel forward/backwards, up/down or angle up/down, minor left/right or up/down angle or other aspects, while selecting others to adjust automatically.

A further aspect of the invention relates to either a seat or bed (e.g., mattress) that employs pressure sensors at various locations that measure the pressure exerted by the seated or reclining/lying occupant. The position of the seat/bed can be adjusted to reduce the amount of pressure at one or more locations or redistribute the weight the occupant and thus redistribute the pressure at one or more locations. In one embodiment the position of the occupant is adjusted such that the pressure at locations with high or maximum pressure is reduced. In another embodiment the weight of the occupant is shifted to reduce the pressure at one or more locations but the ranking of pressure values relative to another location is maintained. For example, if location 1 has a greater value of pressure than location 2, the seat/bed position may be shifted such that while the amount of pressure at location 1 is reduced, it is still greater than the amount of pressure at location 2. Thus, in this aspect of the invention the weight distribution in terms of ranking from highest to lowest pressures are maintained, but the degree or difference between two or more locations remains the same. In this embodiment the seat/bed attempts to eliminate or reduce maximal pressure. In one embodiment the seat/bed adjusts its position to create an average pressure over a plurality of locations of the seat/bed. That is the seat/bed adjusts to reduce the difference in pressure between two or more locations. The above embodiments will have the affect of providing comfort to an occupant with minimal seat/bed position adjustment. Obviously the occupant may shift position and thus redistribute pressures over the seat/bed locations. In one embodiment the seat/bed adjusts on a timed basis. In another embodiment when the occupant redistributes pressures such that a predefined threshold is exceeded, the seat/bed will readjust, either immediately or at a specified or other time thereafter. The seat/bed may be divided into zones defined by one or more of the locations above and adjusted to maintain a average pressure over a zone rather than the entire seat/bed. For example average pressure may be maintained only over the top half or bottom half of a seat/bed; top third, middle third or bottom third of a bed; over a seat bottom, a seat bottom and bottom half of the seat back, a seat back, or otherwise.

All of the equipment necessary to make the above invention is known in the art. For example, beds and seats with adjustable motors are known in the art as are computer and other devices that utilize electrical inputs/outputs to control different functions at different times. Pressure sensors are also well known in the art that can be used or adapted for use in the present invention.

Methods of Playing Video Games:

The present invention relates to methods of playing video games by inputting a code that controls at least one aspect of the game and systems and hardware for carrying out the same. The code is input by a player of the game or an agent thereof.

The identity of the code is not known by the player until it is revealed to him. That is, the code can not be input by a player based on prior knowledge and is not one a player could guess. If the player tried to guess, the attempted code would preferably be close to a random input or at least 1 in 1,000, 1 in 10,000, 1 in 100,000 or at least on in 1 million. The code is not a software application, like a game cartridge/CD, but rather is a security code, login and/or password which allow access to an aspect of a video game. The code can be in the form of symbols, letters, numbers, or alphanumeric. The code can be input into a computer or video game console using an input device such as a standard keyboard or number pad. The code can also be in a computer readable format (CRF). For e.g., the code can take the form of a bar code or a magnetic code such as the magnetic strip on the back of a credit card or on a 3½ inch floppy disk for a computer. The code could be in a CD or DVD format. Methods of writing software and programs of the type necessary to support the present invention is well known in the art.

The video game could be played on a personal computer where the game program is stored on a storage device (such as CD, DVD, or hard drive that is either local, or from a server), from the interne (World Wide Web), or a combination thereof. The game could also be played on a hand held video game device such as a GAME BOY™. The video game could also be played from a home video game console device such as NINTENDO, PLAY STATION I or II, SEGA, X-BOX, etc.

In one aspect, the code does not contain a portion of the game program or software. Instead, the code only permits access to certain aspects or features of a game. The code is an identification code used to identify the player personally or to permit access to an aspect or feature of the game by a person who has access to the code but not others.

The aspects of the video game for which the code provides access can vary. In one aspect, the code provides access to the game itself. That is, without the code, one is not permitted to play the game. This is useful for several applications. In an embodiment, a parent or guardian can limit or control access of a minor to a video game or to particular types of video games by providing the player with a code specific for predetermined games or games with a predetermined rating. The input code could permit a player to play a video game for a specific amount of time for which code encodes. Associated with a code that permits access to a video game for an allotted amount of time is a means which keeps track of the time remaining during multiple intervals of play. Thus, the player may quit the game and play again at a later time(s) using the time remaining at the end of the last play time. This is analogous to a prepaid phone card. The player could obtain a prepaid game card that he uses to gain access to a game(s) for a specific amount of time. The code could also be used to track the activities of a player, such as the number of games, which games, and the time spent player each game is played. The activities are linked to a player account. The player may have a prepaid account or is charged at intervals either in relation to the activities, for the privilege of having access to the games or both.

The code could allow the player to access multiple games. Thus the present invention provides for methods that can be used as a cost effective manner of obtaining access to a wide variety of games without the need to purchase software applications, game cartridges/CDs, etc. Currently, a player purchases an application for a corresponding operating system such as a CD/DVD for a personal computer or a game cartridge/CD/DVD for a gaming device, e.g. PLAY STATION, each time he wants to play a different game. A problem with this is that the player will become board with a game and have to continually buy more software or game cartridges that are new to keep his interest level high enough that he wants to play the game. Instead of buying the full game application, the player could instead buy access to a game application. This would allow the player to play many more types of games than he would have had he purchased the software. In a further embodiment, a player can also avoid the cost of a gaming device, e.g. PLAY STATION, by accessing games over the internet. It is noted that the process of accessing a video game application may involved obtaining software, e.g. on a CRF or by downloading from the internet to a computer, an application that permits or controls access to the game application. This application however, is not a full game application or at least not a complete game application.

In embodiments where the code is on a prepaid game card (the code could be printed or encoded on a magnetic strip), a player could purchase a code which allows a specified amount of access time to a game(s). In an embodiment, the code allows access to multiple games. In an embodiment the games are accessed through the internet. This gives the player different games to choose from with the same code. Control over what types of game are being played could be controlled by giving a player a code that permits access to only a subset of different games. For example, a parent could control access to the games a child plays by giving the child a code that allows a child to play some games but not others, such as games with excess violence. The games can be rated in any appropriate manner. A provider of video gaming devices, software cartridges or an internet site(s) could rate multiple games based on criteria such as violence and then sell access that is limited to a particular category or categories rated or access to the entire selection of games through a code. Instead of buying a gaming device (hardware comprising an operating system) and game applications (cartridges/CD/DVD/etc.), a player simply logs on to an internet site using a code and selects from a range of different games. Preferably, the game selection would change overtime as new or improved games are developed.

In another aspect of the invention, the code allows access to a particular character. For example, different codes could represent different characters. By inputting the code the player becomes a character encoded by the code. The character may be known by the player before inputting the code or not know until the code is input into the game. The codes could also be for different physical parts of a character such as arms, legs, torso, etc. In an embodiment, the physical parts, either all or some, are interchangeable so that different characters can be formed by different combinations of parts. The player could build a character from parts by starting with a base character, no character at all, or by replacing parts on an existing character using multiple codes. The physical parts may impart an advantage over a competitor.

In other embodiments of the invention, the aspect encoded by the code relates to the characteristics of the character of the video game controlled by the player. The character could take the form of an animated human or other character. The character could also be represented by an object, such as a vehicle. The characteristic could relate, e.g., to performance capabilities, offensive capabilities, or defensive capabilities (the various capabilities may overlap).

For performance capabilities, the aspects include increased speed, increased strength, ability to jump or jump higher, increased health, i.e., the ability of the character to survive physical abuse, better vision (day or night), more or intelligence.

Offensive capabilities include weapons, more specifically, a greater number weapons, weapons with faster rate of fire, longer range, more powerful, new types of weapons (e.g., bombs, rockets or missiles, grenades, artillery, cannons, land or water mines, tanks, war planes or ships, other vehicles with mounted weapons, new types of guns such as laser guns, pistols, shotguns, stun guns, rifles, machine guns, rocket-firing guns. Offensive capabilities further include, tips and instructions that are not readily known to a player which give a player an advantage. For example, tips on how to defeat a foe, overcome obstacles, find objects with bonus points, ammunition, or medical supplies. Defensive capabilities include body armor, armored vehicles, protective structures, night vision goggles, additional characters on the player's side, ships, planes, cars, motorcycles or other vehicles, vehicles with better performance such as speed.

In another aspect of the present invention the code is packaged with a product that is not related to a video game device or software, e.g., candy, cereal, clothing, or sporting goods. The product packaged with the code could be used as an advertisement aid to cause customers who buy the product to become interested in the game for which the code is related. Conversely, the code could be packaged with an unrelated product as method of advertising the product to a game player.

Another aspect of the invention relates to a disposable game application software such as a program downloaded from the internet, CD/DVD or game cartridges. In this aspect, the game application allows the player to play the game for a specified amount of time or for a specified number of games. In this aspect the present invention, the disposable software encodes either a portion or all of the game. Once the time of game play or number of games reaches the preset limit, the game application no longer permits the player to play the game. In one embodiment the game software is disposed of or recycled upon expiration of time or games. In another embodiment, the game software is rechargeable and thus can be used again by recharging or adding time or games back to the game application. Additional play time or number of games could be added after expiration of the allotted time (or number of games played), or at any time before expiration. The game application could be recharged, i.e. a disabled application is enabled, through the internet or phone if the game is played on a home computer through a stored game or game on the Internet. This same capability could be combined with a home video game console (hardware with operating system) as well.

Another aspect of the present invention provides for a method of playing a video game on the internet or an internal network (intranet). In this aspect a player may be charged on a per game or unit of time basis. The player is charged a fee on the basis of the number of games played, types of games played, or the amount of play time. A player may play on an internal network or on the internet where a player plays on a shared server. A requirement is that the there must be at least intermittent, direct or indirect communication between the player and the charging entity permitting the charging entity to track play time or number of games played. In one aspect the player's computer/terminal sends signals to the charging entity as to the number of games or time played. In another aspect the player's computer/terminal is passive and is accessed by the charging entity to determine the number of games or time played. The player may set up an account with the charging entity. The player may prepay an account or be billed on based on a time or other interval, e.g., monthly. The billing may be by automatic charging or debiting an account such as a credit card or bank account. In one embodiment the charging entity hosts the game directly thus allowing the charging entity to directly track charges. In another embodiment the player plays at a third party host site. The player's computer/terminal sends signals to the charging entity each time a number of games is played, the amount of play time achieved, or before a game a played. Alternatively, the host server tracks the player's activities and transmits a report to the charging entity. Thus, the charging entity may access the player's activities either directly from the player's computer or through the computer hosting the game, e.g., the host game server. The advantage of this game playing aspect is that it allows a video game provider to shift marketing away from selling game program units to focus on actual number of games or time played. The game provided can provide a player with the most up to date games at less expense to the player and with greater convenience. Players who want to play with other players on different terminals or home computers can all have access to the same version of the game with less upfront expense and more convenience.

For all aspects of the above invention either use existing technology or can be created using the above description and methods well known in the art.

EXAMPLES

Example 1

A parent purchases a prepaid game card and gives it to their child. The card has a code that will allow the child access to games appropriate for his maturity, but not to games the parents feel are inappropriate for the child. The child accesses the internet and a web site where the child can play a video game(s). The child inputs that code and he is allowed to play the game for a specified amount of time. The time remaining during play is tracked through the web site and the child can see how much time is remaining. The child quits the game after a time and come backs the next day to play the game again. The game will allow the child to play the game for the amount of time remaining. The game blocks access by the child once play time has expired.

Example 2

A child buys a box of cereal and a pack of trading cards. Inside the box of cereal and pack of trading cards are codes for a video game. The child turns on his computer and starts a video game stored on his hard drive. He then inputs the code originating from the cereal box and inputs it into the computer as instructed. He finds out his character now has extra ammunition and a more powerful weapon. After finishing the first game, the child turns to another game that relates to the code in his pack of trading cards. Here the code allows the character to have bigger claws and more strength.

Example 3

A game player purchases a disposable video game cartridge for his home video game station. Play time is tracked and subtracted from the time remaining when the game is played. During one game the player scores particularly high and is awarded bonus time. Also during the game the player's character finds bonus time and adds it to the total time remaining. A cable connection and appropriate hardware/software allow the player to recharge the cartridge.

Example 4

A game player obtains a game program in the form of physical software (e.g., CD/DVD) or downloads the game form the internet. The game is provided either free or inexpensively (as compared to game where a fee is charged only to buy the game program) to the player. The player has an account with the game provider (or agent thereof) and when the player plays a game or after a number of games is played (or time played), signals are sent to the game provider who then charges a fee to the player based on the number of games or time played.

Packaging and Method of Packaging Cooking Ingredients:

The present invention relates to packaging of ingredients used in cooking that provides added convenience and time saving. In one aspect the packaging relates to packaging for white granulated, light brown, brown or dark brown sugar or flour. The packaging for a sugar or flour above is aliquotted in ¼/, ⅓, ½, ⅔, ¾ or 1 cup sizes or any combination thereof. Preferred combinations include at least ¼ and ⅓ cup aliquots, ¼ and ½ cup, ½ cup and ⅓ cup, ½ cup and ⅔ cup, or ½ and 1 cup aliquots. In another aspect the aliquot packages are physically connected. In another aspect only aliquots of a single size or measure (e.g., ¼, ⅓, or ½ cup aliquots) are physically connected. Each package may be either re-sealable or not re-sealable. The packaging may be plastic or cellulose based (e.g. paper or cardboard) a combination of plastic and paper or other materials (e.g., plastic or wax lined paper), another suitable material or combination thereof. In one aspect the connected packaged aliquots have a line down the connecting material that is weaker than the surrounding material to allow for easy separation. For example the line could be a perforated line or other means. In this aspect the purpose of this line is to aid in the removal of one aliquot for another. The connected packaged aliquots may be marketed as is or contained within another, second package. This second package may also be plastic, cellulose based (e.g. paper or cardboard) a combination thereof, another suitable material or a combination thereof. The measures of sugar or flour, particularly a brown sugar, may be packaged as a loosely or firmly packed measure. In one aspect the aliquots contain a measuring line for at least one measure less than the full aliquot. For example, a 1 cup or ⅔ aliquot may have a measuring line for ¼, ⅓/or ½ cup. This allows for convenient use of less than a full aliquot. In one aspect, the aliquots are packaged with a larger aliquot such that the outside of the individual aliquots are in contact with the ingredient of a larger aliquot. For example, ½ cup aliquots of firmly packed brown sugar may be packaged in lager package containing a total of 2 or 4 cups brown sugar. For brown sugar, some aliquots may be packed and others not packed.

Methods and Devices for Providing Travel Information to Passengers:

In one embodiment the invention relates to a method of presenting a plane, train, bus, ship or other carrier type passenger with tools for easing travel to unfamiliar destinations. In one embodiment, the invention provides for a method comprising presenting a map of destination terminal to a passenger at the time the boarding pass or ticket receipt is presented. In one embodiment, a suggested route from the arrival gate to a specific connecting gate or concourse, baggage claim or ground transportation is provided.

The present invention further relates to a visual monitoring system on a plane (or train, bus ship or other passenger carrier) that displays information for arriving or departing flights and methods of using the same. In one embodiment the monitors displays gate information for arriving or departing flights. In another embodiment the monitor displays arriving and departure times and flight scheduling information such as delays. In another embodiment the monitor displays baggage claim information (e.g., carousel designation) for the flight. In another embodiment the information is in real time or at least in real time with the monitors inside the terminal or the information is updated with 15 min, 10 min, 5 min or 1 min of real time or the time the information displayed on the terminal monitors. The information may be displayed only after the plane has landed or may be displayed while the plane is in flight. In another embodiment the passenger can input flight information such as city, arrival or departure time, name, flight number, etc. into a device with a monitor, or the monitor itself if it's a touch screen, and the monitor will display pertinent information related to the information input by the passenger. For example the monitor will display the gate, arrival/departure time, any delays, terminal location, etc. for a particular flight. The monitors may be personal monitors associated with each seat or a shared monitor. The monitors may also display a requested map of an airport or terminal or directions to a location such as a gate, baggage, eatery, rental car desk, service desk, shuttle, taxi, bus or other transportation pickup. The map may further provide a suggest route. The present invention preferably uses wireless technology. Methods and equipment for inputting, transmitting and displaying the type of information of the present invention are well known in the art.

Lid for Container and Methods for Reducing Condensation:

The present invention further relates to a lid 200 for the prevention or reduction of condensation of liquids, e.g., water. In one aspect the invention reduces the amount of condensation that collects on the inside of a lid. The lid may be a cover for a container/receptacle e.g., beverage container or cooking utensil such as a pan, pot or skillet. The degree of condensation is decreased by downward facing projections that extend below the surface of the lid. In one embodiment the projections are downward facing convex surfaces 202, e.g., cones or partial spheres (e.g., half-spheres or less than half-spheres). The downward facing projections may be of any shape as shown in FIG. 2E The projections may cover about any integer between 1 and 99% of the inside surface of the lid, e.g., 1, 3, 5, 7, 10, 15, 20, 25, 30, 25, 40, 50, 60, 70, 80, or 90% of the inside lid surface and may be in various configurations as shown in FIG. 2. The shape of the projections is dependent to some extent by the surface tension of the material from which the lid is made. Then projections need to have an angle that is large enough such that condensed liquid will move towards the lowest point of the projection as demonstrated by the small arrows in FIG. 2E and FIG. 2F. The lower the interfacial tension between the material and condensed liquid, e.g., water, the lower the angle can be. The surface area of the projection should be large enough such that the mass of liquid that collects at the apex or lowest point of the projection is great enough to overcome the surface tension and fall from the lid to the inside surface of the container. As the surface area and angle of the projection increases and the interfacial tension between the lid surface and liquid decreases, the rate of liquid return increased. Projections with less than optimal surface area, angle or interfacial tension may also be used however; the rate of liquid return will lower than optimal.

A further embodiment includes a lid that reduces spillage from the edge of the lid when one side of the lid is lifted to a height greater than the height of the opposing side such that the increase in height causes liquid condensed on the bottom surface of the lid to flow to and then off of the outer edge of the lid. In one embodiment the projections are designed such that condensed liquid is directed back to the inside surface of the container as the lid is lifted at an angle, i.e., not maintained at a horizontal position as when it is removed. Normally, when a lid without downward facing projections is removed by lifting the lid at an angle greater than horizontal, the condensed liquid moved towards the lowest position. This lowest position is usually the edge of the lid. The condensed liquid then falls from the edge of the lid and down the outer side of the container or onto the surface surrounding the container. Downward facing projections that inhibit the condensed liquid from moving towards the lowest point (the bottom edge of the lid) when one side of the lid is raised will cause the liquid to build up in mass to a point where forces are overcome and the liquid falls to the inner surface of the container rather than down the outer side of the container surface (FIG. 2F). The lid has a central horizontal cover portion 201 and is normally adapted 208 to matingly engage the upper peripheral edge 209 of a container so as to selectively maintain said lid in a covering relationship on said container. In one embodiment the spillage reducing downward projection comprises a first wall 211 depending downwardly from the inside of the cover portion 201, said first wall having a terminal end below the surface of said cover portion 201; a second wall 212 merged with the terminal end of said first wall, said second wall extending upwardly in an outwardly spaced apart relationship to said first wall so as to merge with the said horizontal cover portion 201 or portion adapted 208 to matingly engage the upper peripheral edge of a container. The ring may extend the entire circumference 213, partial circumference, or the entire circumference but intermittently divided by sections with a reduced or absence of downward angle in order to maintain strength and integrity of the lid surface. For example, the lid may further comprise a plurality of spaced apart radially extending ribs connecting said first wall and said second wall, said ribs cooperating with said first wall and said second wall to define downwardly depending arcuate spillage reducing means. The ring is typically encircled by the edge of the container when mated with said container and is in close proximity (normally less than 1 cm, more preferably less than 5 mm, even more preferably less than 2 mm) to the container edge so as to minimize spillage of the container contents between the edge of the lid and edge of the container. In a preferred embodiment the projection to reduce spillage between the lid edge and container edge has a longitudinally arcuate configuration or ring-shaped 213 and follows the contour of the inner lid edge. The ring or partial ring is on the inner side of the container that contacts the lid. For example, the ring or partial ring is on the inside of the edge of the container 209 (e.g., cup, pot, etc.) that contacts the lid such that condensed liquid falls from the lid and into the inner surface of the container rather than between the lid and the outer surface of the container. Often the edge of the container rests in a grove which acts to the keep the lid in place. When this is the case, the inner surface of the lid is lower than the top most portion of the grove. In these circumstances, the downward facing projections, such as a ring, are in relation to the inner lid surface and thus lower than the inner surface of the lid horizontal cover.

In one aspect of the present invention, if two identical containers are filled half full with a liquid (e.g., water) at it's boiling point or filled with the liquid and heated to its boiling point, when a smooth inner surface lid is attached to one container and a comparable lid with downward facing projections of the present invention is attached to the second container (lids are not attached securely if no vent is present), the lid of the present invention will collect at least 10% less, 25% less, 50% less or at least 75% less condensed liquid than the lid with the smooth inner surface. Moreover, once the rate of transfer of condensation between the liquid surface and lid has reached equilibrium, the rate of rate of return of condensed liquid of the lid of the present invention is at least 10%, 25%, 50% greater than comparable lid with a smooth inner surface. For lids with a The depth of the projections or the distance between the lowest point of the projection and the surface immediately surrounding the projection may vary depending on the factors discussed herein. In one aspect a projection may extend about 1, 2, 3, 4, 5, 6, 7, 8, 9, 10, 11, 12, 13, 14, 15, 16, 17, 18, 19, 20 25, 30, 35, 40, 50, 70, 80 or 100 mm, is less than about 1, 2, 3, 4, 5, 6, 7, 8, 9, 10, 11, 12, 13, 14, 15, 16, 17, 18, 19, 20 25, 30, 35, 40, 50, 70, 80 or 100 mm, or is greater than about 1, 2, 3, 4, 5, 6, 7, 8, 9, 10, 11, 12, 13, 14, 15, 16, 17, 18, 19, 20 25, 30, 35, 40, 50, 70, 80 or 100 mm.

In another embodiment the lid comprises at least 1, 2, 3, 4, 5, 6, 7, 8, 9, 10, 11, 12, 13, 14, 15, 16, 17, 18, 19, 20 25, 30, 35, 40, 50, 70, 80, 100, 250, 500, or 1000 projections. In another embodiment projections that act as wave dampening baffles extending below the surface of the lid around the base of the raised vent pedestal 203, projections surrounding a portion of the lid that acts as part of an opening for removing liquid from the container (e.g., a tear away portion on the horizontal cover portion which can be made into a flexible hinged flap 204), as part of support structures for increasing lid rigidity, as weakened areas for easy separation or opening (such as on the horizontal cover portion for making a hinged flap 210), and for stacking are excluded from the present invention.

Another embodiment relates to a lid designed to be attached to a cup or mug, e.g., a disposable cup or travel mug with an improved opening from which the user drinks from the cup or mug. The current lid designs are such that the upper lip of the drinker normally comes into contact with the side edges of the horizontal cover portion 210 adjacent to the opening in the lid 204 when drinking from the container. When the beverage is hot the drinker's lip is burned or is made uncomfortable by the heat transferred through the lid or by the hot beverage itself pouring through the opening adjacent to horizontal cover side portions. By making the opening 204 larger, the drinker's upper lip will not contact the side edges of the horizontal cover portion and will avoid burns. This is especially useful when the horizontal cover is thin (e.g., less than 2 mm, 1 mm, 0.75 mm, 0.5 mm or 0.25 mm thick) or otherwise poor insulator of heat. Current cup lid openings have a distance 205, measured straight across from the apex/corners formed by the horizontal cover portion side edge 210 and the edge of the container 214, which is about 27 mm or less. For lids with a tear line or scored/weakened lines 206 used to facilitate tearing of the lid to make a flap opening, the distance between the two tear lines is about 27 mm or less. Thus, the present invention provides for a lid for a container containing a hot beverage with a pre-made opening 205 or tear lines that form an opening 205 that is at least 27 mm across, at least 30 mm, at least 33 mm, at least 35 mm, at least 37 mm, at least 40 mm, at least 45 mm, at least 50 mm, at least 55 mm, at least 60 mm, at least 65 mm or at least 70 mm across.

Methods that can be used for making the lids of the present invention are well known in the art. For example, a plastic disposable lid can be made by blow or injection molding. In one embodiment the lid is a plastic disposable for use with a disposable cup made of paper, Styrofoam® or other material.

Toy Figure with Magnet in Dorsal Side/Posterior Portion:

The present invention relates to toy figures that contain magnets and are thus capable of magnetically interconnecting with ferromagnetic surfaces and other similarly constructed figures. The toy figures have more stability in a seated position when brought into contact with a seat comprising a metal structure or a magnet. Thus, the toy of the present invention is less likely to need adjustment in seating position or fall over than a toy without a magnet.

The prior art is replete with different types of toy figures. Toy figures typically fall within one of three major categories. The first category of toy figures includes stuffed figures, such as rag dolls. The second category of toy figures includes plastic action figures, such as Barbie® dolls. The third category of toy figures includes molded wire frame figures. Magnets are sometimes used in the hands of stuffed dolls to provide the stuffed dolls with the ability to join its hands together.

In an exemplary embodiment of the present invention is that of a toy person. However, it will be understood that the figure could be that of an alien, a monster, an animal or any other common toy figure configuration.

The toy figure comprises a dorsal/posterior side which includes a dorsal element selected from a back, buttocks, a back of a head, a back of a leg(s), or a corresponding or equivalent dorsal/posterior structure of a toy figure.

Embedded or incorporated in one or more of the dorsal elements is a magnet or ferrous metal (if the toy seat contains a magnet). The magnets can be selectively attached to any ferromagnetic surface, such as a metal seat. Further included in the present invention is a toy seat (bench, chair, car seat, etc.) with a magnet (or ferrous metal if the toy contains a magnet) embedded or incorporated in it. The magnet is oriented in a manner compatible with the magnets in the toy figure.

Further included in the present invention is a combination of a toy figure with a magnet embedded or incorporated in one or more of the dorsal elements selected from the back, buttocks, a back of a head, a back of a leg(s), or a corresponding or equivalent structure of a toy figure and a toy seat with a magnet embedded or incorporated in it, and wherein the magnet in the toy figure and the seat are oriented in a compatible manner.

The magnet may be of any suitable type although in one embodiment the magnets are rare-earth magnets.

The invention further relates to a method of stabilizing a toy figure in a seated position by using embedding or incorporating a magnet in the dorsal side of the toy figure and placing the toy figure in a seated position on a toy seat. A further embodiment of the method is wherein the seat comprises a metal structure or a magnet and wherein a magnetic force is created between the toy and the seat.

Device for Sterilizing or Disinfecting Fomites:

The present invention further relates to a device form sterilizing fomites and methods for using the same. In this aspect, the fomite is sterilized using a UV light source that is either built into the fomite or is intimately associated therewith. According to the present invention, the UV light exposes the outer surface of the fomite from the inside or inner surface of the fomite. The UV light passes through the fomite's inner surface and directly contacts the infectious agent/microorganism on the outer surface. Accordingly, the material separating the UV light from the surface must be transparent or at least partially transparent to UV light. In another embodiment, the material between the UV light and fomite surface is "doped" or contains (e.g., as a mixed composition or layer) quantum dots/nanoparticles, phosphors or other materials which can shift a wavelength or range of wavelengths of the electromagnetic spectrum through upconversion or downconversion. In one embodiment, the surface material of the target fomite comprises quantum dots which up-converts or down-converts a first wavelength of light to a second wavelength, wherein the first wavelength is not between 250-260 nm and the second wavelength is between 250-260 nm. However, the end wavelength that directly contacts the microorganism is within the UV range, preferably about 250-260 nm or more preferably about 254 nm.

As used herein, the term "fomite" (foe-mite) means an inanimate physical object that serves to transmit an infectious agent from person (or animal) to person (or animal). For example, a door handle with virus particles or bacteria resting on its surface would be a fomite. The term fomite should not to be confused with a vector, which is an organism that transmits the infection (as in mosquitoes transmit malaria parasites). Specific examples of fomites included in the present invention include a: door handle/knob, light/lamp switch, telephone, toilet handle, faucet and faucet handles, drinking fountain handle and mouth guard/spray shield, computer keyboard or mouse, and a push button such as on an elevator, atm, or vending machine. Each of the same may also be individually excluded from the present invention.

The UV light is preferably UV-C or within the range of 240-290 nm, preferably between 250-260, more preferably about 254 nm. The UV light can travel from the inside of the object and pass from the inside through the outside surface. As the light passes through the outside surface it kills the microorganisms on the outside surface of the fomite.

This reduces unwanted exposure by persons inhabiting the space. Preferably the distance of open space the UV light must travel before striking the target fomite is less than 25 cm, 15 cm, 10 cm, 9 cm, 8 cm, 7 cm, 6 cm, 5 cm, 4 cm, 3 cm, 2 cm, 1 cm, 9 mm, 8 mm, 7 mm, 6 mm, 5 mm, 4 mm, 3 mm, 2 mm or less than 1 mm. The UV light can also be transmitted from a distant source and delivered to the inner surface of the fomite or within the distance above through the use of UV fiber optics. Because the UV light travels from inside the fomite through the outside surface of the target fomite, the solid material between the inside and outside surfaces of the target fomite much be transparent or partially transparent to UV light.

In one embodiment of the present invention a shield is not present between the outer surface and the space inhabited by persons. The reason for this is because of the short time of UV light exposure required to sterilize or at least partially disinfect the outer surface. Because the intensity of UV light increases in relation to distance by the inverse of the square, the UV intensity also drops precipitously as the distance from the outer surface increases. For example, the UV intensity decreases by half as the distance between the UV light source and surface doubles. When the distance is tripled, the intensity decreases by a factor of nine. The prior art has not appreciated the fact that UV light can be directed from the inside of an object directly to its outer surface without the potential harm to inhabitants near the object. In one aspect of the present invention, a UV light source at 254 nm wavelength delivers at least 2000, 3000, 4000, 5000, 6000, 7000, 8000, 9000, 10,000, 11,000, 12,000, 13,000, 14,000, 15,000, 16,000, 17,000, 18,000, 19,000, 20,000, 21,000, 22,000, 23,000, 24,000, 25,000 microwatt sec/cm$^2$ of UV light energy to the target area or fomite surface. The UV light energy in microwatt sec/cm$^2$ can be delivered in a time of a) less than about, b) equal to about, or over a time c) longer than about: 0.25 sec, 0.5 sec. 0.75 sec, 1 sec, 2 sec, 5 sec, 10 sec, 15 sec, 30 sec, 45 sec, 1 min, 2 min, 3 min, 5 min, 7 min, 10 min, 15 min, 20 min, 30 min, 40 min, 50 min, 1 hr, 2 hr, 3 hr, 4 hr, 5 hr, 6 hr, 7 hr, 8 hr, 9 hr, 10 hr, 11 hr, 12 hr, or 24 hr. The longer the time over which the necessary UV energy is delivered, the lower the intensity needed. The lower the energy, the closer inhabitants can be to the fomite's outer surface without potential harm. In one embodiment, the UV energy is delivered such that an inhabitant can safely be within a distance of 6 inches, 1 foot, 3 feet, 5 feet, 7 feet, 9 feet, 10 feet, 15 feet or 20 feet from the fomite surface.

To deliver a particular dose of UV light energy, the device and methods of the present invention utilize a means of regulating the time the UV light source is turned on. This is normally carried out by a timer that controls an electrical switch. In another embodiment the timer is activated by use of the object. For example, the turning of a door knob/handle, movement of a light switch to an on or off position, turning of a faucet handle. The UV light can be turned on at the time the object is used or something thereafter. Preferably, the timer is set with a delay such that a period of time elapses before the UV light is turned on. This gives time for the user to break contact with the object. For example, the turning of a door knob/handle may activate the system which begins with a time delay. Once the user has time to step away from the handle, the UV light source is activated and the fomite surface is disinfected. The timer then turns off the UV source until the system is once again activated. In another embodiment the system turns on the UV source at a particular preset time. For example, the UV light source may be turned on at night or other times when there is less likely to be inhabitants nearby.

Figure 3B:
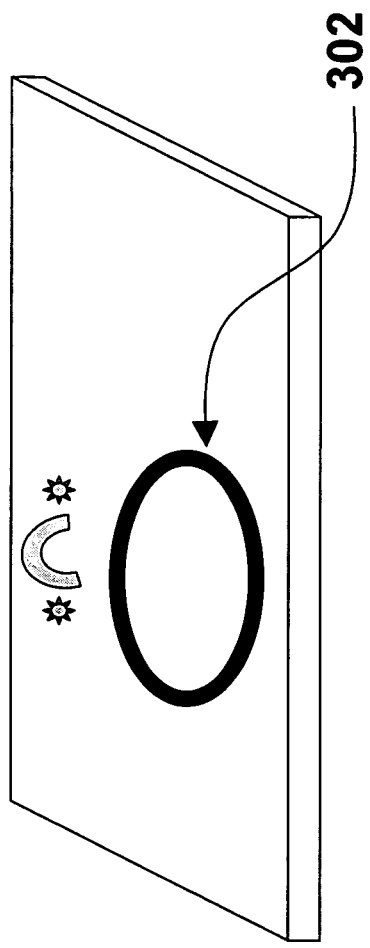
Figure 3C:
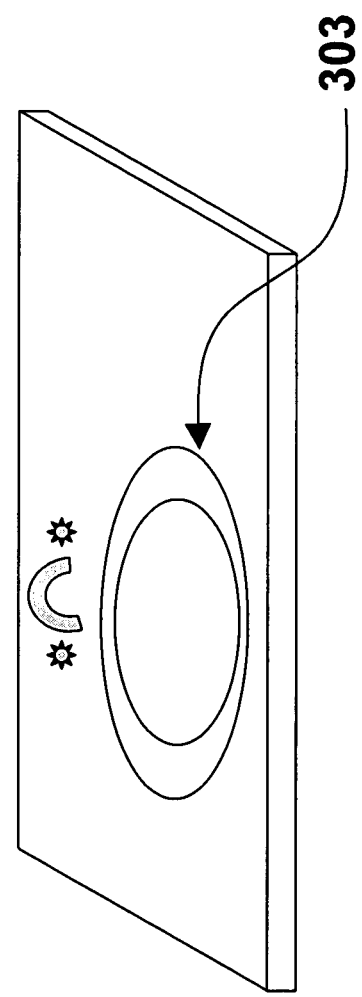
Figure 3D:
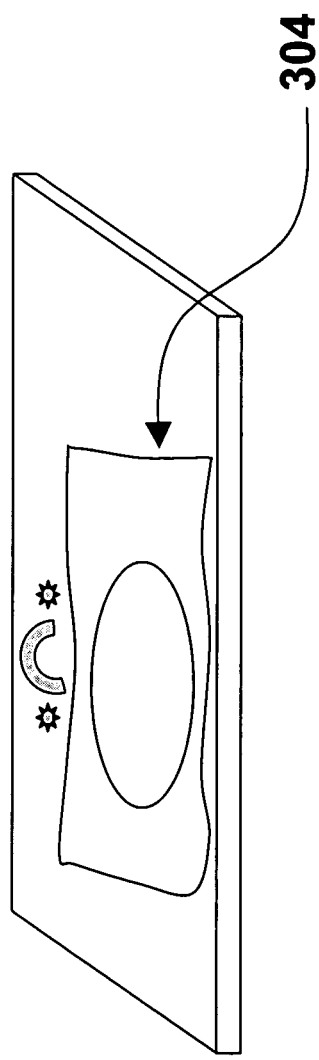
Figure 3E:
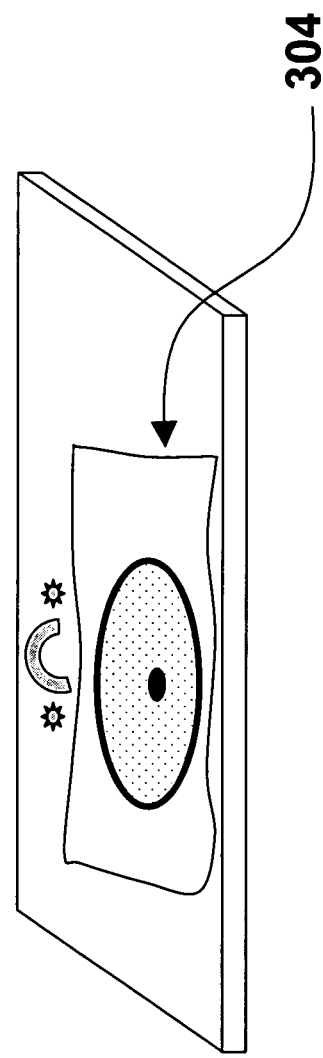
Figure 3J:
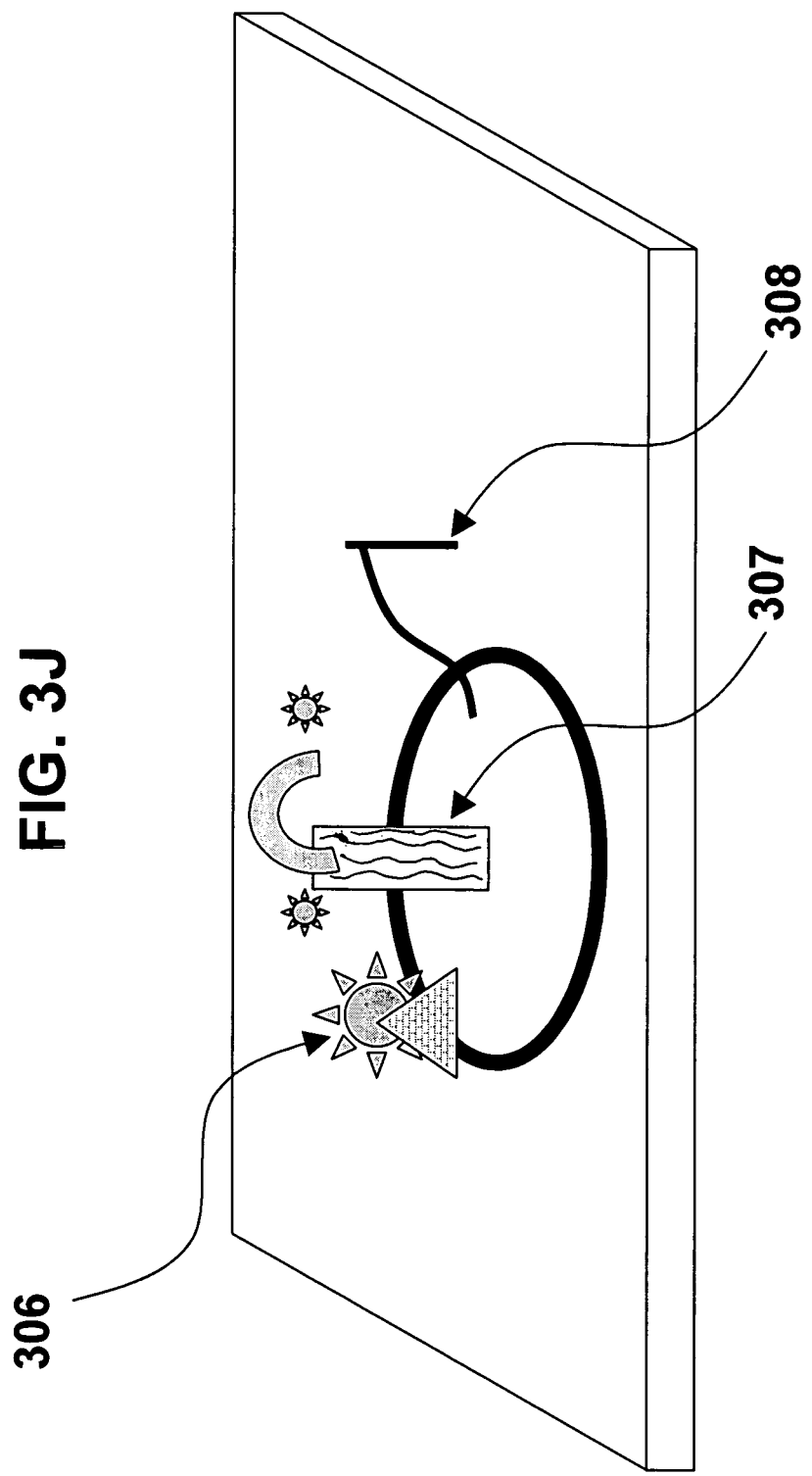

Liner for Sink to Create a Playful Environment:

The present invention relates to a cover or liner for a sink, counter top or both to make the sink conducive for play and methods of using the same. The liner may only cover the concave portion of a sink 300 (e.g., FIG. 3B and FIG. 3F), may extend to cover at least a portion of the surrounding horizontal surface (countertop) 301 (e.g., FIG. 3C, FIG. 3D and FIG. 3G-I), or may cover only or mainly the countertop (FIG. 3E). The liner may flexible and pliable sheet (single or multilayer) of material such as plastic or rubber (e.g., FIG. 3H) that conforms to the shape of the sink when placed therein. The liner may be semi-ridged in that a portion of the liner conforms to the shape of the sink or a portion thereof (e.g., FIG. 3I). The liner may further be ridged such that it fits within the sink, but is pre-shaped to conform or partially conform to the shape of the sink (e.g., FIG. 3F, FIG. 3G and FIG. 3I).

Accordingly to the present invention the liner has either a 2-dimensional surface ornamentation, a 3-dimensional ornamentation or both. A 2-dimensional surface ornamentation is a pattern or drawings on the surface. A 3-dimensional surface ornamentation comprises structures that project outward from the surface of the liner. Surface patterns/drawings include drawings that represent the surface or bottom of an ocean, pond, lake, creek, stream, river, pool or other body of water, a beach, roads, houses, cars, people, water slides and ground effects such as grass, rocks, water, sand, dirt, trees, shrubs, etc. Three dimensional surface ornamentation or projections include trees, palms, water mills 306, waterfalls 307, water slides 308, houses, cars, rocks, people and other outside play equipment and building structures such as houses or huts, swing set, slide, merry-go-round, jungle gym, other play equipment, or other objects. The three dimensional objects may be packaged with but do not physically attach to the liner. The objects may also be packaged separately for use with the liner. The objects may be temporarily affixed or removable from the liner such as with the use of peg-hole, Velcro®, snaps, ties, suction cups or other fastener means or they may be permanently attached. The objects may be attachable/attached to the portion of the liner that fits within the sink or the portion that covers the countertop.

The liner is particularly designed for children. The liner is placed in a sink and a child can play make believe based on the scene set by the liner. For example, the liner could be a beach, tropical island, water park, house with a swimming pool, ocean, lake, pond, a pit filled with things such as water, quick sand, lava, a play goo, etc.

In one embodiment the liner extends beyond the outside edge or lip of the sink 304. Thus the scene can be extended beyond just the depressed portion or cavity of the sink to the counter top. Preferably the extension is sufficient to prevent slippage of the liner into the sink such that is collapses onto itself. Fasteners or other securing devices may also be included to secure the liner in place. The fasteners can attach the liner to the sink or countertop.

The liner may further be water tight and may further contain a stopper, plug or other means for storing and releasing liquids such as water 305. The liner may be combined with a pump to circulate water. The pump for example, could circulate water over a play waterfall, watermill or water slide. The liner may also be combined with other objects such as a vehicle including a car, boat, or personal watercraft, toy people or animals, toy buildings or structures such as houses or huts, or trees, palms or other plants or natural objects. The liner may also be combined with a device that covers the faucet or a portion or that is place behind the water stream of the faucet to give the appearance of a waterfall when the water is turned on. The waterfall is typically an elongated piece of plastic or other material, preferably rectangular, that comprises a design or ornamentation of a waterfall or at least flowing water or has a blue or partially blue background that gives color to water flowing over the object. The waterfall may be attachable to a faucet 307 or sink by any appropriate means such as by fasteners that attach or clamp the waterfall to the faucet, such as the fasteners above. The liner may also be combined with a means for diverting water from the faucet to another object. For example a tube or hose can divert water to create a waterslide, waterfall or watermill.

The liner and objects attached thereto of combined therewith are preferably plastic, rubber or other material that is not damaged by water. Further the materials preferably are non-toxic and do not shatter or break into sharp fragments with dropped.

Education Method and Learning Tools for Use Therein

One of the challenges of teaching students is maintaining a high level of interest in, and a high level of retention of, the subject matter taught. Rote memorization of facts is ineffective because it is boring. Rote memorization further leads to a low level of retention because the student has not formed a context into which the facts can be logically framed.

"Hands on" or "wet" laboratory experiments are often useful in maintaining a student's interest and providing a context or framework from which facts can be placed. A drawback of this approach is that the experimentation process can be time consuming and expensive. Moreover, experiments a student can perform are limited by their knowledge of the subject matter and their technical expertise in the field making the experimentation less personally relevant to the student.

There is therefore a need in the art of education for novel methods of teaching a selected subject matter, and learning tools to be used therein, wherein the student is taught using data from experimentation of scientists or researchers in the field of study.

The present invention relates to a method of teaching, and learning tools for use therein. The method comprises the steps of: teaching a student how to interpret particular aspects of raw data of a research experiment, having the student perform the interpretation, and using the interpreted data and the experience of interpreting the data to form a context in which to introduce and learn new subject matter.

The invention further relates to tools used in the teaching method, wherein the tool comprises the data that is interpreted by the student in the method of teaching.

The invention further relates to bookmarks or other articles comprising a polynucleotide sequence.

The invention further relates to a game for teaching a particular subject matter or merely for entertainment.

The present invention relates to a method of teaching, and learning tools for use therein. The method comprises the steps of: teaching a student how to interpret particular aspects of raw data of a research experiment, having the student perform the interpretation, and using the interpreted data and the experience of interpreting the data to form a context into which new subject matter is introduced and learned.

Typically, in the method of the present invention, a student is presented with a set of raw data from a scientific experiment. The term "raw" means that the data from an experiment has not been fully analyzed. That is, some further step(s) of calculation or interpretation is required to determine the precise meaning of the results. The data, for example, may be in the form of numerical values that need to be inserted into a mathematical formula and calculated to interpret the results of the particular experiment. The data may also be in the form where the result in consistent or inconsistent with a hypothesis or theory. The data may be qualitative or quantitative. The data may further represent a physical characteristic(s) of a molecule.

Typically, the ability to perform the experiment from which the raw data is generated is an experimental procedure that is beyond the technical expertise or intellectual capabilities of the average student at the particular level in question, or beyond the beyond the physical and financial resources of the student or, more likely, the teaching institution. The experiment may be beyond the technical capabilities of the student because of the use of dangerous equipment or chemicals needed to perform the experiment, or involve complex or numerous steps not appropriate for the age or class setting of the student. The experiment may relate to concepts beyond the general understanding of the class or require the learning of concepts not appropriate for the class setting. The subject matter of the experiment may further not be consistent with the subject matter of the class or the concepts may not relate closely enough to the subject matter of the class to be appropriate. For example, to carry out the experiment the student, who may be a high school (grades 9-12), junior high (grades 7 and 8), or elementary student (grades 1-6) may need to have a general understanding of college undergraduate or graduate level mathematics, chemistry (e.g., organic, physical, analytical, or molecular or cellular biology, microbiology, botany or other biological science. The experiment may further require large and/or expensive equipment that is inappropriate or impractical for the class setting. The experimentation may also involve experimentation on animals. Thus, the present invention provides a method of learning science without the ethical considerations the go with animal experimentation. For example, students can avoid procedures that would be painful or lethal to an animal and avoid euthanasia of animals. It also avoids the need for the physical and monetary resources required to purchase, handle, and maintain Although performing the experiment may be beyond the capabilities or intellect of the student, the goal, purpose, or end result of the experiment should be such that it is understandable and appropriate for the subject matter of the class. For example, it may be inappropriate for a student to perform an experiment on a polynucleotide to determine its base pair sequence, i.e., sequencing a polynucleotide such as DNA. It may further be beyond the intellectual capabilities of a student to understand the fundamentals or mechanisms of the experiment. In many instances however, it would be appropriate and within the intellectual capabilities of the students to teach them the general molecular structure of the DNA, i.e., that it is made up of 4 bases A, T, G and C arranged in such a fashion as to make up our genetic code. In this case, it would also be appropriate and within the intellectual capabilities of the students to teach them how to interpret the raw data obtained from an experiment to sequence DNA.

For example, the raw data normally obtained from an experiment to sequence DNA is bands (a term of art referring to thin rectangular shaped areas on a substrate containing DNA of a particular size) on an electrophoresis gel which is detected using autoradiography or f. In autoradiography, the bands emit light or radioactivity which exposes X-ray film. When the film is developed, the bands of DNA are represented as dark bands on a lighter background. The bands are staggered and each band represents a particular base (A, T, G or C) at a particular position in the DNA sequence. By determining the order of the bands, the sequence, and therefore molecular structure, of a specific DNA molecule is identified.

For example, a student is presented with an image resulting from a DNA sequencing experiment in which the raw data comprises bands representing different lengths of DNA are ordered in lanes. Each consecutive band represents a species of DNA with that differs by a single base in length. For example, if the first band represents DNA that is 100 bases in length, the second band represents DNA that is 101 in length, the third band represents DNA that is 102 bases in length, and so on. The base type (A,G,C, or T) is determined by the lane where the band is found. For example, a band representing DNA 100 bases in length in the lane reserved for "A's" means that the DNA has an "A" at position 100. If the next band, representing DNA 101 bases inength is in the lane reserved for "G's", then the sequence for the DNA at positions 100 and 101 would be "A" and "G", respectively. Alternatively, the raw data could be in the form of an electropherogram where the different sizes of DNA are represented by peaks on the electropherogram and further wherein each base type (A,G, C, or T) is represented by a different color line.

Normally, the raw data is actual experimental data, although it of course may be copied or replication for mass production. Alternatively, the raw data is simulated to either look like or represent the original raw data. Whether as a workbook, book, or separate sheets, embodiments of the present invention include these articles of manufacture wherein at least 10%, 20%, 30%, 40%, 50%, 60%, 70%, 80%, 90%, or 95% or 100% of the examples contain in part or whole raw data.

In a preferred embodiment of the present invention the raw data is from a biological experiment. The data could be in the form of numerical values from a scientific instrument measuring, for example, the level of radioactivity, luminescence, fluorescence, mass, light wavelength, temperature, force, speed, pH, salinity, concentration, number of samples (e.g., number of cells or number of colonies), etc. The raw data can also be qualitative in nature where the variable, such as those above, are measured in a relative fashion, for example, the presence or absence of something. In a preferred embodiment, the raw data interpreted is in the form of identifying the presence or absence of biological matter such as a eukaryotic or prokaryotic cell, polypeptide, polynucleotide, or antibody. In a more preferred embodiment, the raw data interpreted is the presence of a polynucleotide. In a further preferred embodiment the raw data is the presence of a polynucleotide of a particular length, for example a band of DNA from a PCR reaction, restriction enzyme digest, or sequencing reaction separated by gel electrophoresis, a Southern blot, Northern blot or Western blot, ELISA, radioimmunoassay. The raw data could also be from a chemistry or physics experiment. For example, the data could be from NMR, IR Spectroscopy, Raman Spectroscopy, calorimetry (DSC), thermogravametric analysis (TGA), chromatography (solid phase, FPLC, HPLC), or x-ray diffraction (powder or single crystal).

In a further preferred embodiment, the DNA is from either a prokaryote or eukaryote. More preferred, the DNA is from an animal. Still more preferred the animal is a kind of animal selected from the group consisting of: a farm animal, an animal normally seen at a zoo, an exotic species, is an animal threatened by extinction, or is an endangered animal, and is an extinct animal, such as a wooly mammoth. Still more preferred, the animal is selected from the group consisting of: dog, cat, human, lizard, bird, cow, pig, horse, sheep, horse, lion, zebra, tiger, leopard, cheetah, rhinoceros, elephant, chimpanzee, gorilla, giraffe, kangaroo, hippopotamus, wolf, coyote, bobcat, mountain lion, frog, turtle, snake, fish, salamander, squirrel, chipmunk, mouse, rat, rabbit, raccoon, opossum, goat, whale, seal, bear, dolphin, guinea pig, hamster, alligator, crocodile, and gerbil. In the case where the animal is extinct, such as a dinosaur, the sequence may be simulated. That is, the sequence is not that of any known species or is from an extant species but is referred to in the answer portion of the media as being from an extinct. There may be more than one simulated sequence representing different genes, different body parts, different extinct species. For example, a student may be given raw data from a sequencing gel and instructed how to determine the sequence. Once the student determines the sequence, the next task would be to determine which "extinct" species it came from. The student determines whether the task of determining the sequence was performed properly by comparing his answer to sequences in a database, whereby each sequence represents a species of animal. If there is a match then the student is informed that he performed the task properly by showing the species represented by the sequence. Mismatches, or errors in the sequences, may also be indicated. Thus, the student would be shown the closet matched sequences and the bases where the errors occurred displayed.

The present invention further relates to articles of manufacture for use as learning tools in the methods of the present invention, in other methods, or just as a novelty. The learning tools are forms of media, typically paper, cardboard, plastic or other articles wherein said tools comprise the raw data, in a readable or visual form, used in the learning method. The media may also be in the form of computer readable media, such as a CD ROM or web page, wherein the raw data is read or visualized on a computer monitor. The tools may be photographs, photocopies, or other reproducible images of the raw data. The raw data may comprise a page or pages in a textbook or a portion thereof. The raw data may also be supplied in a supplement to the textbook, such as a workbook or as a handout on sheet(s) of paper or other appropriate media. The raw data may further comprise information on a computer monitor or web page on the world wide web. The raw data may be supplied on more unconventional forms of media such as trading cards or bookmarks, clothing (e.g., T-shirt).

Instructions on how to interpret the raw data, the actual raw data, and the answers to the interpretation of the raw data may be provided together, separately or provided on separate forms of media. For example, the raw data and instructions on how to interpret the raw data may be supplied on conventional readable media, such as paper (i.e., a hard copy), and the answers supplied from a computer readable form, such as a web page. Under this scenario the student would interpret raw data supplied on a hard copy of readable media and then check his answer using the computer via a web page. The raw data may involve more than one step of interpretation and the student may be required to use separate forms of media to complete the steps. For example, the student may interpret the sequence of a polynucleotide by interpreting the bands on a gel as described above. The student may further be required to interpret the sequence to determine the source of the polynucleotide, i.e., the species of the organism or the gene from which the polynucleotide was obtained. For example, the student may complete a first step of determining the sequence of the DNA and then a second step of comparing the sequence to multiple sequences in a database, e.g., GenBank or other database, preferably web based, to determine the gene or the species from which the polynucleotide was obtained.

In an embodiment, a person with the raw data, such as a DNA sequence from a gene, is instructed to go on the interne to a particular web site. At the web site, data is entered and the answer to a question, such as what is the origin of the DNA sequence, is provided. Alternatively, the student can choose a selection from a menu or index that references the raw data in some fashion such as by the name of the species, a code or by using all or a portion of the raw data. Further, the web site may provide additional information on the species from which the DNA sequence is from or something more broadly related, such as endangered species in general. The site could also provide information on scientific experimentation and technology. The site could provide the person with methods of conducting experiments at home or other science related activities.

In a preferred embodiment, the raw data is visualized on a bookmark as the kind normally used to mark a page in a book. Preferably the raw data is a polynucleotide sequence including DNA or RNA sequences. Typically, the bookmark comprises a flat elongated member (rectangular) having a first end, a second end spaced apart from the first end, a first edge, a second edge spaced apart from the first edge a middle region situated between the first and second ends, a first side, and a second side facing away from the first side, and with raw data being situated in the middle region of the flat elongated member. The bookmark may further be made of a pliable material and/or be made of a compressible material (e.g., paper, cardboard or plastic). The bookmark may further include a decorative ornamentation, for example, at one of the sides or ends. The bookmark may further comprise a hole at one of the ends and may further comprise a string or ribbon attached or tied to the bookmark using the hole. The raw data can also be visualized on other articles of manufacture including writing utensils such as pens and pencils, notepads and notebooks such as spiral bound notebooks, binders such as 3 and 4 ring binders, purses, bookbags and the like, clothing such as ties, T-shirts, hats and scarves, as decorative covers, cups, mugs, bottles, etc. In one embodiment, the name of the species from which the raw data is derived is associated with the article, preferably printed on or packaged therewith.

Another aspect of the present invention relates to a method whereby an article directs a person to a web site containing information relating to a subject of the article. In one embodiment the method is used to further educate a person regarding a subject of the article. In one embodiment the subject is animals and the article is related an biological organism (e.g., plant, animal, bacteria, fungi or virus). In one embodiment the article comprises raw data, a picture of an animal, contains the name of an animal or is in the shape of an animal. In one embodiment the animal is a species listed above. In one embodiment the animal is protected or endangered. In one embodiment the article is a coffee mug, an article of clothing (e.g., sweatshirt, T-shirt, etc.), a key chain, a charm, or a toy (e.g., a toy animal) or figurine. In one embodiment the web site in printed on or is packaged with the web site URL.

In another aspect the invention relates to an article comprising a biological material. The biological material may be nucleic acid (RNA or DNA), protein, cells or particles. If the biological material is cells or particles or other infectious material it is 100% killed or inactivated, i.e., harmless. The biological material is enclosed and isolated from the environment. The biological material may be in a liquid such as a preserving agent or may be encapsulated in a solid material such as glass, Lucite®, plastic, etc. The biological material may be part of a novelty or article of utility such as a pen, pencil, charm, ring, necklace, cup, mug, bottle, glass, figurine, toy, article of clothing, etc. In one embodiment the biological material is derived from a pathogenic organism such as a bacteria or virus. Examples include HIV, ebola, *Bacillus anthraces, Clostridium botulinum, Variola major, Yersinia pestis*, flu virus, cold virus, HSV, *Treponema pallidium, Gonorrhea*.

The present invention further relates to a new board game where the object is to be the first to construct a species (e.g., dinosaur) DNA sequence, skeleton, body, etc. This may be a 1, 2, 3, 4, 5, 6 or more player board game.

Each player gets a game piece holder (e.g., hard plastic strip) with a unique DNA sequence on it, referring to various types of dinosaurs or other species. There will be sets of matching game pieces in the form of DNA sequences, possibly written as AGCT etc., broken up into smaller sections, which can be won as the player moves around the board game, which will fit into sections along the players' game piece holder (e.g., DNA strips that match portions of game piece holder).

There will be 'dummy' DNA sections, which do not match any of the species (e.g., dinosaur) sequences in the game.

The game will be won when someone gains all his/her matching sections of DNA strips and completes the DNA sequence by filling the game piece holder for their chosen species. Pieces of DNA will be won as the players move round the board game by throwing dice and moving the equivalent number of spaces on the board. Different spaces will either benefit or set back the players.

Players may be allowed an option to trade spare or other DNA pieces, if they land on a certain space which states this or directs the player to a card which does the same. Players can, for example, ask to change 1, 2, 3 or more pieces depending on the space they land on. The other player may be obliged to swap.

Setbacks: setbacks to the players could be landing on a space, which represents a volcanic eruption, earthquake, rain storm or other event which covers or interrupts the dig and makes you lose a piece of matching DNA. If you have no matching DNA segments yet, you will lose 2 pieces of non-matching strips back to the game piece holder.

An earthquake or other event could halt your dig for some time and 1, 2 or more turns at throwing the dice could be lost. Amateur paleontologists, for e.g., could have ruined the dig and contaminated the DNA, players lose 1, 2, 3 or more pieces of matching DNA, or non-matching if no matching has been collected. Landing on a meteor space, for e.g., more than 3 times, by the same person will result in them being ejected from the game, since their dinosaur will become extinct.

Benefits: benefits to the players could be landing on a space, which represents a bonus, e.g., good weather forecast for two weeks, which lets them collect 1, 2, 3 or more pieces of DNA segment, due to increased work completed. Another complete skeleton is found at the dig, this could benefit the player by 1 piece. A huge downpour exposes a new skeleton, making it easier to dig and the player gains 2 pieces. A rich benefactor, for e.g., donates money to add more workers to the dig, this allows the player to get 1, 2, 3 or more throws of the dice in a row.

Cards: Cards, e.g., bone shaped, with helpful or detrimental instructions on them, would be collected by landing on certain spaces.

Game piece holder: The DNA segments, matching and non-matching, may be kept for example, inside a molded plastic volcano, set in the middle of the board. The opening at the top of the volcano will be large enough for a hand to reach in to get a DNA segment piece but will conceal the identity of the pieces. This will stop players being able to select the correct segment for their DNA strip.

The board may be decorated and colored with scenes and environments, which would be appropriate to a dig. The spaces referring to volcanoes etc, should be decorated according to the description and instructions.

The (bone) cards would be made of cardboard, hard plastic, or other suitable material, and shaped as to stack on top of each other to sit on a section on the board.

Player pieces may be bones, skulls, claws, or paleontologists, in differing positions.

Hard plastic dinosaur representations may be included for each of the dinosaur strips. This may be a representation, which is in one piece, or one which is built a little at a time as matching DNA segments are gained. If pieces are lost a piece of the representation would be taken off.

The player who wins will be able to place the representation of their dinosaur on the board. This means they have enough DNA to bring their dinosaur back to life!

In an alternative embodiment, the DNA pieces are replaced with pieces representing different bones (fossils) with the object of the game being to be the first to complete the skeleton of a species (e.g., dinosaur).

In a further alternative embodiment, the pieces represent different part of the species (e.g., dinosaur) such as legs, head, neck, tail, back, ribs, etc. with the object being to be the first to construct a complete species. The parts may all have to be from a single species or may be interchanged with other species to form "new" species.

In a further alternative embodiment, the game is in an electronic format for a personal computer, stationary video game device or portable hand-held electronic game device.

What is claimed is:

1. A system for reducing the size of an email account, said system comprising:
   a) an email server;
   b) an email program;
   c) a data file storage system;
   d) a system for matching a sender and a recipient with a common data file storage location on said data file storage system;
   e) a system for moving or copying and saving a selected computer readable data file to said common data file storage location on data file storage system;
   f) a system for alternatively determining whether said recipient is to receive either an email message comprising a link to said computer readable data file stored at said data file storage location on data file storage system or an email message comprising said computer readable data file attached thereto;
   g) a system for alternatively, generating a link to said computer readable data file stored at said data file storage location on data file storage system and inserting said link into said email message when said sender and said recipient are matched to said common data file storage location, or attaching said computer readable data file to said email message when said sender and said recipient cannot be matched to said common data file storage location, before said email message is sent to said recipient.

2. The system of claim 1, wherein said common data file storage location is chosen by said recipient.

3. The system of claim 1, wherein said common data file storage location is unknown to said sender.

4. The system of claim 1, comprising a system for moving or copying and saving said computer readable data file to a different file storage location for each of two or more recipients, wherein said link to said selected computer readable data file is unique for each of said two or more recipients.

5. The system of claim 1, wherein said link does not show said data file storage location in a sent email message of said sender.

6. A method of using a system to provide a recipient of an email message access to a computer readable data file selected by a sender, said method comprising the steps of:
   i) determining whether said sender and said recipient are matched with a common data file storage location on a data file storage system;
   wherein, if said sender and said recipient are matched with a common data file storage location on a data file storage system, then performing the steps of;
   ii) moving or copying and saving said selected computer readable data file to said common data file storage location on said data file storage system;
   iii) generating a link to said selected computer readable data file; and,
   iv) inserting said link into said email message before said email message is sent; and,
   v) sending said email message containing said link to said recipient; and,
   wherein, if said sender and said recipient are not matched with a common data file storage location on a data file storage system, then performing the steps of;
   vi) attaching said selected computer readable data file to said email message; and,
   vii) sending said selected computer readable data file to said recipient as an attachment to said email message.

7. The method of claim 6, wherein said recipient chooses said common data file storage location.

8. The method of claim 6, wherein said common data file storage location is unknown to said sender.

9. The method of claim 6, wherein said computer readable data file is moved or copied and saved for each of two or more recipients, wherein said data file storage location is different for each of said two or more recipients, wherein said link to said computer readable data file is generated for each of said two or more recipients, and wherein said link is unique for each of said two or more recipients.

10. The method of claim 6, wherein said link sent to said recipient does not show the data file storage location in a sent email message of said sender.

11. A system for removing a computer readable data file attached to an incoming email message and saving said attached computer readable data file at a data file storage location on a data file storage system separately from said email message, wherein said system functions independent of a sender of said email message, said system comprising:
   a) an email server;
   b) an email program;
   c) said data file storage system;
   d) a system for determining whether said sender and said recipient are matched with said common data file storage location on said data file storage system;
   e) a system for removing said attached computer readable data file from said incoming email message and saving said computer readable data file to said data file storage location on said data file storage system;
   f) a system for generating a link to said computer readable data file and inserting said link into said incoming email message.

12. The system of claim 11, wherein said data file storage location in on said recipient's computer.

13. The system of claim 11, wherein said data file storage location in on a file server.

14. A method of using a system to remove a computer readable data file attached to an incoming email message and save said attachment to a data file storage location on data file storage system separately from said email message, said method comprising the steps of:
   i) matching a recipient with said data file storage location on said data file storage system;
   ii) removing said attached computer readable data file from said incoming email message;
   iii) saving said computer readable data file to said data file storage location on said data file storage system;
   iv) generating a link to said computer readable data file; and,
   v) inserting said link into said email message before said email message is delivered to said recipient.

15. The method of claim 14, wherein said data file storage location in on said recipient's computer.

16. The method of claim 14, wherein said data file storage location in on a file server.

* * * * *